US012577522B2

(12) United States Patent
LeDuc et al.

(10) Patent No.: US 12,577,522 B2
(45) Date of Patent: Mar. 17, 2026

(54) SYSTEM AND METHOD FOR SCREENING THERAPEUTIC AGENTS

(71) Applicants: Carnegie Mellon University, Pittsburgh, PA (US); University of Pittsburgh—Of the Commonwealth System of Higher Education, Pittsburgh, PA (US)

(72) Inventors: Philip LeDuc, Wexford, PA (US); Li Wan, Pittsburgh, PA (US); Carola Neumann, Pittsburgh, PA (US); John Skoko, Pittsburgh, PA (US); Jun Yin, Pittsburgh, PA (US); Mei Zhang, Pittsburgh, PA (US)

(73) Assignees: Carnegie Mellon University, Pittsburgh, PA (US); University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 665 days.

(21) Appl. No.: 17/325,593

(22) Filed: May 20, 2021

(65) Prior Publication Data

US 2021/0363477 A1 Nov. 25, 2021

Related U.S. Application Data

(60) Provisional application No. 63/027,397, filed on May 20, 2020.

(51) Int. Cl.
| | |
|---|---|
| *C12M 1/34* | (2006.01) |
| *C12M 1/00* | (2006.01) |
| *C12M 1/12* | (2006.01) |
| *C12M 1/32* | (2006.01) |
| *C12M 3/00* | (2006.01) |

(52) U.S. Cl.
CPC ............ *C12M 41/46* (2013.01); *C12M 21/08* (2013.01); *C12M 23/12* (2013.01); *C12M 25/14* (2013.01); *C12M 45/06* (2013.01)

(58) Field of Classification Search
CPC ...... C12M 41/46; C12M 21/08; C12M 23/12; C12M 25/14; C12M 45/06
USPC ...................................................... 435/287.1
See application file for complete search history.

(56) References Cited

U.S. PATENT DOCUMENTS

| | | | | |
|---|---|---|---|---|
| 11,235,330 | B2 * | 2/2022 | Hansen | ................. B01D 71/82 |
| 2006/0014273 | A1 * | 1/2006 | Yasuda | ................. C12M 25/02 |
| | | | | 435/297.5 |
| 2009/0041825 | A1 * | 2/2009 | Kotov | ................. C12N 5/0647 |
| | | | | 435/29 |

(Continued)

OTHER PUBLICATIONS

Abbott, "Biology's new dimension", Nature, 2003, pp. 870-872, vol. 424.

(Continued)

*Primary Examiner* — Michael L Hobbs
*Assistant Examiner* — Lenora A Abel
(74) *Attorney, Agent, or Firm* — The Webb Law Firm

(57) ABSTRACT

A drug screening device is provided. A method of determining optimal drug concentrations and efficacy in a patient using the device are provided. A method of determining effective chemotherapeutic drugs and effective concentrations thereof using the device is provided. Also, a method of determining safety and efficacy of drugs using the device is provided.

15 Claims, 21 Drawing Sheets

(56)                    References Cited

U.S. PATENT DOCUMENTS

2019/0187129 A1*    6/2019  Skardal .................. G01N 33/58

OTHER PUBLICATIONS

Asghar et al., "Engineering cancer microenvironments for in vitro 3-D tumor models", Mater Today (Kidlington), 2015, vol. 18:10, pp. 539-553.

Begley et al., "Raise standards for preclinical cancer research", Nature, 2012, vol. 483, pp. 531-533.

Bhattacharjee et al., "The upcoming 3D-printing revolution in microfluidics", Lab Chip, 2016, vol. 16, pp. 1720-1742.

Cappetta et al., "Doxorubicin targets multiple players: A new view of an old problem". Pharmacological Research, 2018, vol. 127, pp. 4-14.

Chang et al., "Parallel Microfluidic Chemosensitivity Testing on Individual Slice Cultures", Lap Chip, 2014, pp. 4540-4551.

Chou et al., "Computerized Quantitation of Synergism and Antagonism of Taxol, Topotecan, and Cisplatin Against Human Teratocarcinoma Cell Growth: a Rational Approach to Clinical Protocol Design", Journal of the National Cancer Institute, 1994, vol. 86:20, pp. 1517-1523.

Chou, "Theoretical Basis, Experimental Design, and Computerized Simulation of Synergism and Antagonism in Drug Combination Studies", Pharmacological Review, 2006, vol. 58:3, pp. 621-681.

Chou, "Drug Combination Studies and Their Synergy Quantification Using the Chou-Talalay Method", Cancer Research, 2010, vol. 70:2, pp. 440-446.

Croce et al., "Autofluorescence spectroscopy and imaging: a tool for biomedical research and diagnosis", European Journal of Histochemistry, 2014, vol. 58:2460, pp. 320-338.

Culbertson, et al. "Diffusion coefficient measurements in microfluidic devices", Talanta, 2002, vol. 56, pp. 365-373.

Emadi et al., "Cyclophosphamide and cancer: golden anniversay", Nature, 2009, vol. 6, pp. 638-647.

Esch et al., "Organs-on-chips at the frontiers of drug discovery", Nature, 2015, vol. 14, pp. 248-260.

Fisher et al., "Increased Intensification and Total Dose of Cyclophosphamide in a Doxorubicin-Cyclophosphamide Regimen for the Treatment of Primary Breast Cancer: Findings From National Surgical Adjuvant Breast and Bowel Project B-22", Journal of Clinical Oncology, 1997, vol. 15:5. pp. 1858-1869.

Ganz et al., "Long-Term Follow-Up of Cardiac Function and Quality of Life for Patients in NSABP Protocol B-31/NRG Oncology: Doxorubicin and Cyclphosphamide (AC) Followed by Paclitaxel With AC Followed by Paclitaxel and Trastuzumab in Patients With Node-Positive Breast Cancer With Tumors Overexpressing Human Epidermal Growth Factor Receptor 2", Journal of Clinical Oncology, 2017, vol. 35:35, pp. 3942-3950.

Gelmon et al., "Phase I/II Trial of Biweekly Paclitaxel and Cisplatin in the Treatment of Metastatic Breast Cancer", Journal of Clinical Oncology, 1996, vol. 14:4, pp. 1185-1191.

Hachey et al., "Applications of Tumor Chip Technology", Lab Chip, 2018, vol. 18:19, pp. 2893-2912.

Hosseini et al., "Bio-inspired microstructures in collagen type I hydrogel", Journal Biomed Mater Research Part A, 2015, vol. 103A, pp. 2193-2197.

Huh et al., "From 3D cell culture to organs-on-chips", Trends in Cell Biology, 2011, vol. 21:12, pp. 745-754.

Huh et al., "Microengineered physiological biomiimicry: Organs-on-Chips", Lab Chip, 2012, vol. 12, pp. 2156-2164.

Kashaninejad et al., "Organ-Tumor-on-a Chip for Chemosensitivity Assay: A Critical Review", Micromachines, 2016, vol. 7:130, pp. 1-24.

Kirson et al., "Chemotherapeutic treatment efficacy and sensitivity are increased by adjuvant alternating electric fields (TTFields)", BMC Medical Physics, 2009. vol. 9, pp. 1-13.

Kolesky et al., "Three-dimensional bioprinting of thick vascularized tissues", PNAS, 2016, vol. 13:12, pp. 3179-3184.

Kolesky et al., "3D Bioprinting of Vascularized, Heterogenous Cell-Laden Tissue Contsructs", Advanced Materials, 2014, vol. 26, pp. 3124-3130.

Kumar et al., "Preclinical screening methods in cancer", Indian J Pharmacol, 2016, vol. 48:5, pp. 481-486.

Lawson et al., "The Cleared Mammary Fat Pad Transplantation Assay for Mammary Epithelial Organogenesis", Cold Spring Harb Protoc, 2015, vol. 12, pp. 1-8.

Lee et al., "Three-dimensional culture models of normal and malignant breast epithelial cells", Nat Methods, 2007, vol. 4:4, pp. 359-365.

Loessner et al., "Bioengineered 3D platform to explore cell-ECM interactions and drug resistance of epithelial ovarian cancer cells", Biomaterials, 2010, vol. 31, pp. 8494-8506.

Lori et al., "Doxorubicin and syclophosphamide for the treatment of canine lymphoma: a randomized, placebo-controlled study", Vet Comp Oncol, 2010, vol. 8:3, pp. 188-195.

Ma et al., "Biomimetic tumor microenvironment on a microfluidic platform", Biomicrofluidics, 2013. vol. 7, pp. 1-13.

Matthews et al., "Mathematical Methods of Physics (Appendix only)", 2nd Edition, 1979, W.a. Benjamin, Lebanon , Indiana, USA.

Mehndiratta et al., "Diagnostic Techniques and Surgical Management of Brain Tumors, Chapter 2—Brain Tumour Imaging", InTech, 2011, pp. 27-42.

Motlagh et al., "Fluorescence properties of several chemotherapy drugs: doxorubicin, paclitaxel and bleomycin", Biomedical Optics Express, 2016, vol. 7:6, pp. 1-7.

Muller et al., "Precise measurement of diffusion by multi-color dual-focus fluorescence correlation spectroscopy", EPL, 2008, vol. 83, pp. 46001-p1-46001-p5.

Murphy et al., "3D bioprinting of tissues and organs", Nature Biotechnology, 2014, vol. 32:8, pp. 773-785.

Nakada et al., "Chemosensitivity testing of ovarian cancer using the histoculture drug response assay: sensitivity to cisplatin and clinical response", Int J Gynecol Cancer, 2004, vol. 15, pp. 445-452.

Nguyen et al., "Biomimetic model to reconstitute angiogenic sprouting morphogenesis in vitro", PNAS, 2013, vol. 110-17, pp. 6712-6717.

Pampaloni et al., "The third dimension bridge the gap between cell culture and live tissue", Nature Review Molecular Cell Biology, 2007, vol. 8, pp. 839-845.

Reddy, "Dietary Fat and Colon Cancer: Animal Studies", Lipids , 1992, vol. 27:10, pp. 807-813.

Rosati et al.. "A Phase II Study of Paclitacel/Cisplatin Combination in Patients With Metastic Breast Cancer Refractory to Anthracycline-Based Chemotherapy", Tumori, 2000, vol. 86, pp. 207-210.

Skardal et al., "A Reductionist Metastasis-on-a-Chip Platform for In Vitro Tumor Progression Modeling and Drug Screening", Biotechnol Beoeng., 2016, vol. 113:9, pp. 2020-2032.

Sohn et al.. "Paclitaxel and Cisplatin Combination Chemotherapy in Pretreated Breast Cancer", Cancer Research and Treatment, 2003, vol. 35:3, pp. 267-273.

Sokol et al., "Growth of human breast tissues from patient cells in 3D hydrogel scaffolds", Breast Cancer Research, 2016, vol. 18:19, pp. 1-13.

Sparano et al., "Phase II Trial of Biweekly Paclitaxel and Cisplatin in Advanced Breast Carcinoma: An Eastern Cooperative Oncology Group Study", J. Clin Oncol., 1997, vol. 15, pp. 1880-1884.

Szot et al., "3D in vitro bioengineered tumors based on collagen I hydrogels", Biomaterials, 2011, vol. 32:31, pp. 7905-7912.

Tibbit et al., "Hydrogels as Extracellular Matrix Mimics for 3D Cell Culture", Biotechnology and Bioenginnering, 2009, vol. 103:4, pp. 655-663.

Wan et al., "Mimicking Embedded Vasculature Structure for 3D Cancer on a Chip Approaches through Micromilling", Scientific Reports, 2017, vol. 7:16724, pp. 1-8.

Wan et al., "Tumor-on-a-chip for integrating a 3D tumor microenvironment:chemical and mechanical factors", Lab Chip, 2020, vol. 20, pp. 873-888.

Yuanlong et al., "Characteristic Autofluorescence for Cancer Diagnosis and Its Origin", Lasers in Surgery and Medicine, 1987. vol. 7, pp. 528-532.

(56) References Cited

OTHER PUBLICATIONS

Zhao et al., "Off-the-shelf microsponge arrays for facile and efficient construction of miniaturized 3D cellular microenvironments for versatile cell-based assays", Lab Chip. 2013, vol. 13, pp. 2350-2358.

\* cited by examiner

```
clear all;
range=40;% length between two parallel channels
dx=0.1;% distance interval
pi=3.1415;
C=zeros(1,range/dx);%vector for drug concentration
dt=0.001;%time interval D=1.635;%Diffusion coefficient of drug
coe=D*dt/(dx*dx);% diffusion coefficient
tumorp=[1,100,200,300,400];%tumor positions
C(1)=10;%initial concentration value
T=1/dt;
P=[48];%time range, 48 indicates 48 hours
m=1;

for i=1:T*P(m)

C(1)=10; %iteration for initial point, constant injection; for one time injection, C(1)=C(1)-D*dt*(C(1)-
C(2))/dx;

for j=2:range/dx-1

C(j)=C(j)+coe*(C(j+1)-2*C(j)+C(j-1)); %general iteration, Forward Euler
        C(j)=C(j)-0.000001;
        if C(j)<0
            C(j)=0; %ensure concentration stays positive.
        end
    end C(range/dx)=C(range/dx)+D*dt*(C(range/dx-1)-C(range/dx))/dx; %iteration for endpoint end for l=1:5
    tumorC(l)=C(tumorp(l));  %concentration at each tumor position
end plot(C);%concentration profile
```

FIG. 4

A
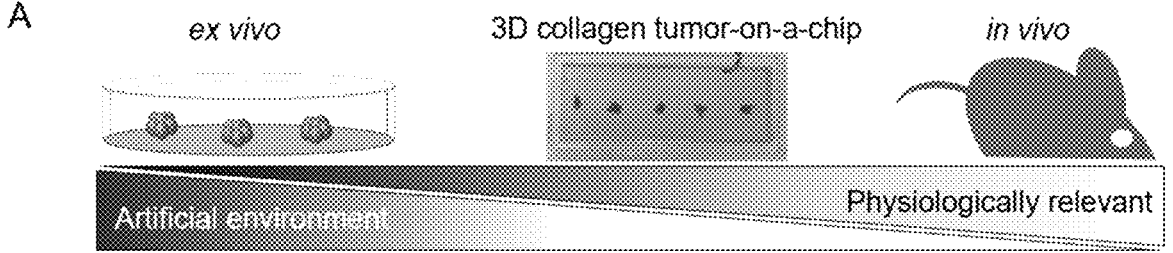
B
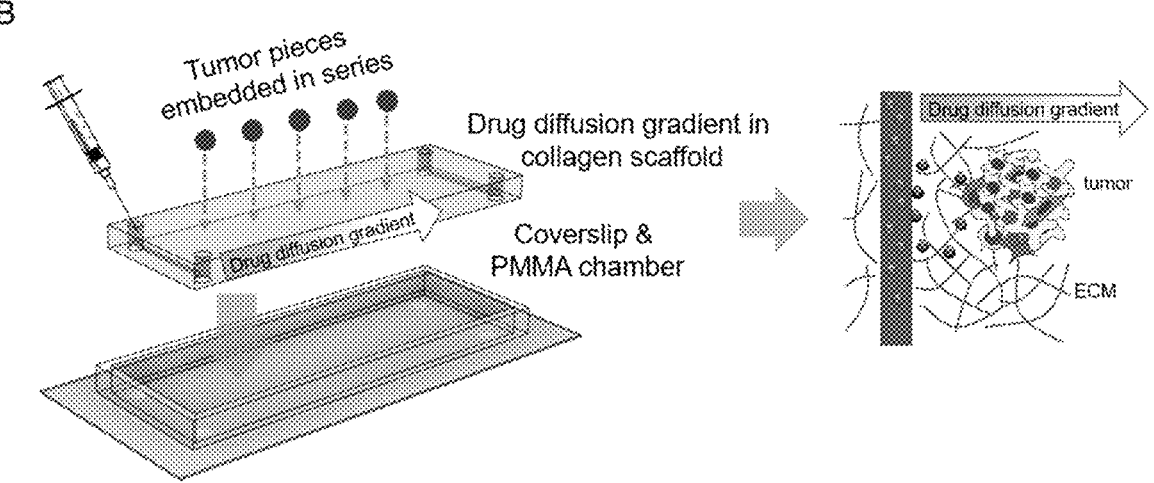
FIG. 5

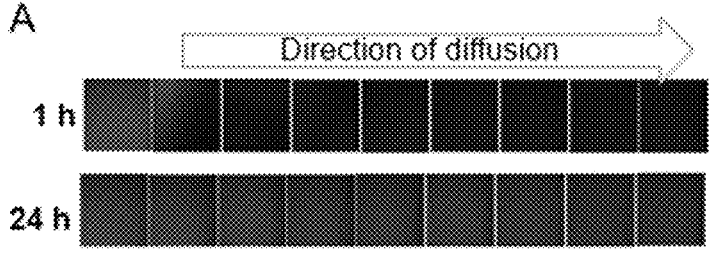
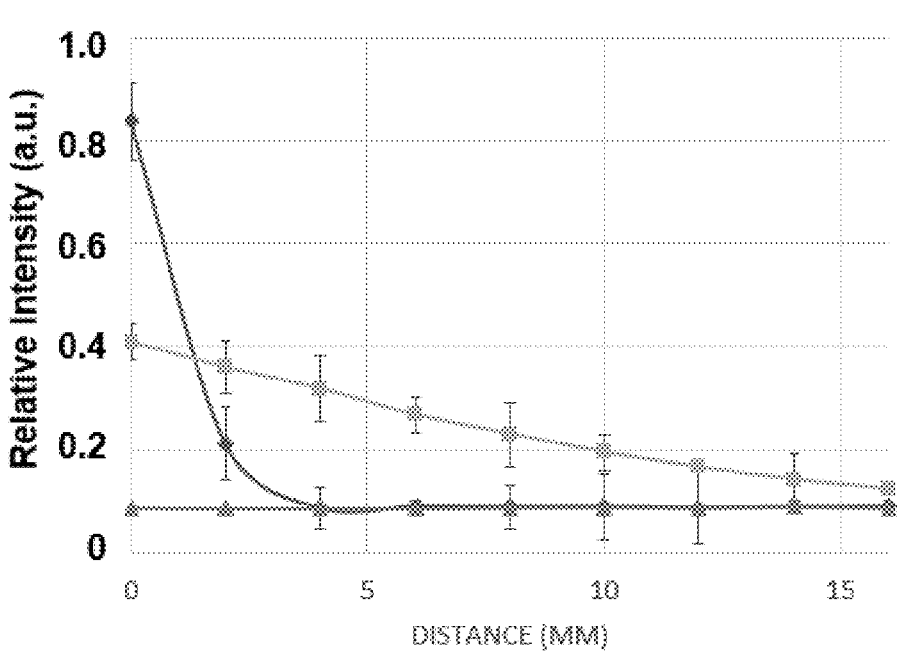
FIG. 6A

C

D

E

A

*para (doxo+cyclo)*

| Doxo dose | Cyclo dose | Effect | CI |
|---|---|---|---|
| 1000.0 | 1000.0 | 0.565 | 0.88483 |
| 466.0 | 590.0 | 0.539 | 0.65745 |
| 142.0 | 280.0 | 0.493 | 0.463368 |
| 25.8 | 107.0 | 0.32 | 1.64364 |
| 3.0 | 49.0 | 0.239 | 1.65633 |

*oppo (doxo+cyclo)*

| Doxo dose | Cyclo dose | Effect | CI |
|---|---|---|---|
| 1000.0 | 49.0 | 0.552 | 0.80553 |
| 466.0 | 107.0 | 0.503 | 0.87403 |
| 142.0 | 280.0 | 0.483 | 0.53806 |
| 25.8 | 590.0 | 0.393 | 1.57837 |
| 3.0 | 1000.0 | 0.451 | 1.0542 |

B

*para (doxo+cyclo)*

| Doxo dose | Cyclo dose | Effect | CI |
|---|---|---|---|
| 1000.0 | 1000.0 | 0.618 | 0.67149 |
| 466.0 | 590.0 | 0.617 | 0.32376 |
| 142.0 | 280.0 | 0.585 | 0.1904 |
| 25.8 | 107.0 | 0.468 | 0.35184 |
| 3.0 | 49.0 | 0.423 | 0.16408 |

*oppo (doxo+cyclo)*

| Doxo dose | Cyclo dose | Effect | CI |
|---|---|---|---|
| 1000.0 | 49.0 | 0.603 | 0.85132 |
| 466.0 | 107.0 | 0.559 | 0.92351 |
| 142.0 | 280.0 | 0.584 | 0.19408 |
| 25.8 | 590.0 | 0.45 | 1.01488 |
| 3.0 | 1000.0 | 0.451 | 1.0998 |

FIG. 8A

C
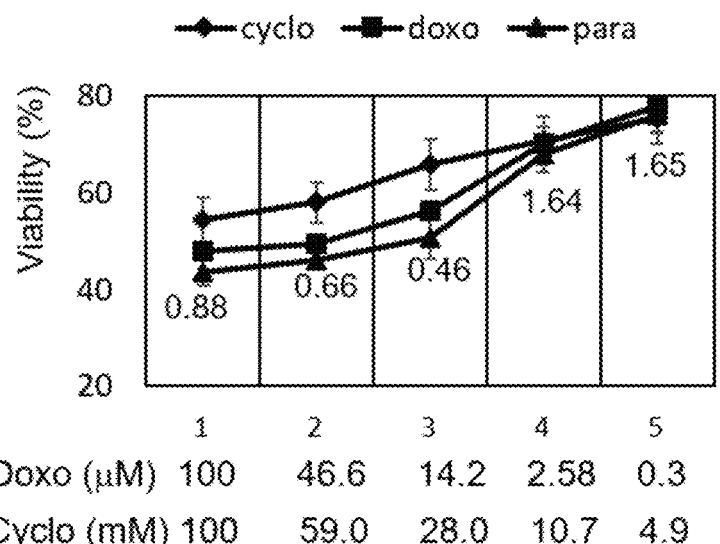
| | 1 | 2 | 3 | 4 | 5 |
|---|---|---|---|---|---|
| Doxo (μM) | 100 | 46.6 | 14.2 | 2.58 | 0.3 |
| Cyclo (mM) | 100 | 59.0 | 28.0 | 10.7 | 4.9 |
D
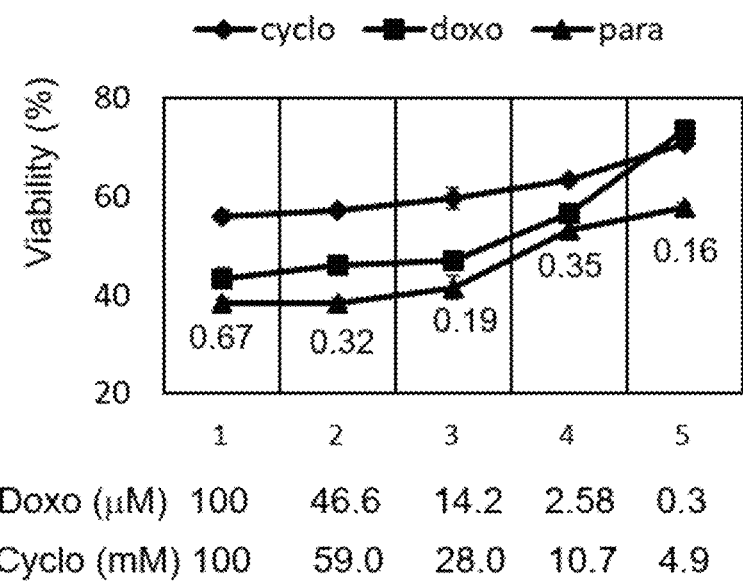
| | 1 | 2 | 3 | 4 | 5 |
|---|---|---|---|---|---|
| Doxo (μM) | 100 | 46.6 | 14.2 | 2.58 | 0.3 |
| Cyclo (mM) | 100 | 59.0 | 28.0 | 10.7 | 4.9 |
FIG. 8B

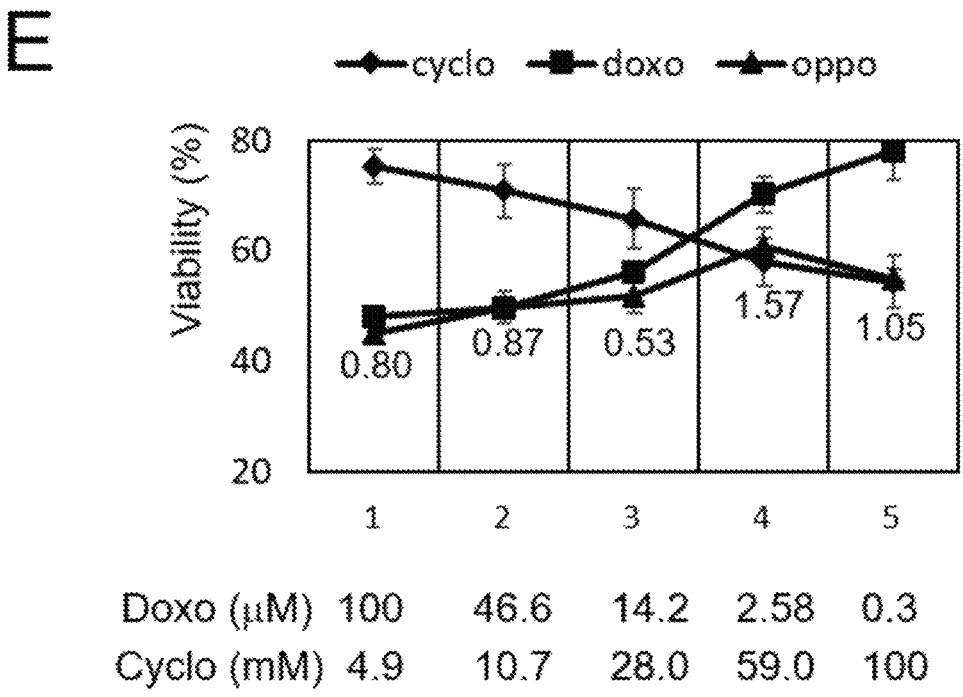
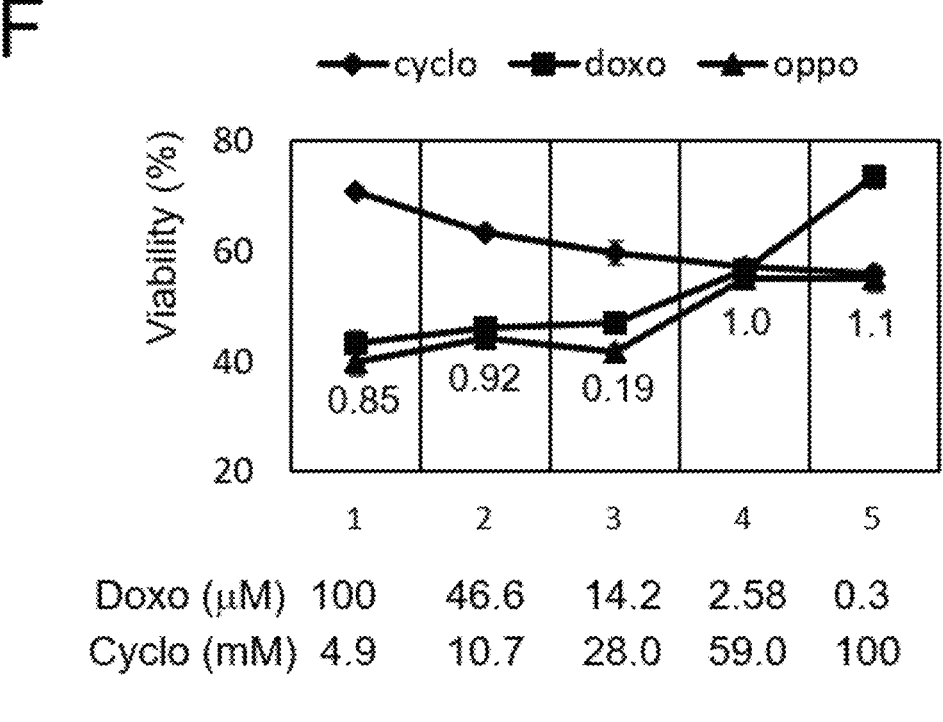
FIG. 8C

A

| Doxo dose | Effect | | Cyclo dose | Effect | |
|---|---|---|---|---|---|
| 3.0 | 0.22 | | 49.0 | 0.246 | |
| 25.8 | 0.3 | | 107.0 | 0.292 | |
| 142.0 | 0.439 | | 280.0 | 0.342 | |
| 466.0 | 0.504 | | 590.0 | 0.421 | |
| 1000.0 | 0.52 | | 1000.0 | 0.457 | |
| | | | | | |
| X-int: 2.73547 | | | X-int: 3.25177 | | |
| Y-int: -0.6773 +/- 0.04155 | | | Y-int: -1.0299 +/- 0.04469 | | |
| m: 0.24759 +/- 0.01938 | | | m: 0.31670 +/- 0.01835 | | |
| Dm: 543.842 | | | Dm: 1785.55 | | |
| r: 0.99093 | | | r: 0.99500 | | |

B

| Doxo dose | Effect | | Cyclo dose | Effect | |
|---|---|---|---|---|---|
| 3.0 | 0.265 | | 49.0 | 0.292 | |
| 25.8 | 0.435 | | 107.0 | 0.367 | |
| 142.0 | 0.531 | | 280.0 | 0.404 | |
| 466.0 | 0.539 | | 590.0 | 0.429 | |
| 1000.0 | 0.567 | | 1000.0 | 0.439 | |
| | | | | | |
| X-int: 2.3468 | | | X-int: 3.39923 | | |
| Y-int: -0.4849 +/- 0.07779 | | | Y-int: -0.6860 +/- 0.08711 | | |
| m: 0.21701 +/- 0.03629 | | | m: 0.20182 +/- 0.03578 | | |
| Dm: 171.663 | | | Dm: 2507.46 | | |
| r: 0.96051 | | | r: 0.95596 | | |

| Cis dose | Effect | | Pac dose | Effect | |
|---|---|---|---|---|---|
| 27.0 | 0.277 | | 0.001 | 0.26 | |
| 75.0 | 0.316 | | 0.1 | 0.301 | |
| 240.0 | 0.353 | | 24.0 | 0.369 | |
| 560.0 | 0.471 | | 270.0 | 0.414 | |
| 1000.0 | 0.538 | | 1000.0 | 0.472 | |
| | | | | | |
| X-int: 2.94716 | | | X-int: 4.51759 | | |
| Y-int: -0.8923 +/- 0.12093 | | | Y-int: -0.2862+/- 0.01791 | | |
| m: 0.30278 +/- 0.05130 | | | m: 0.06335 +/- 0.00773 | | |
| Dm: 885.438 | | | Dm: 32930.1 | | |
| r: 0.95953 | | | r: 0.97837 | | |

FIG. 10A

| Doxo dose | Effect | | Pac dose | Effect | |
|---|---|---|---|---|---|
| 27.0 | 0.248 | | 0.001 | 0.1 | |
| 75.0 | 0.231 | | 0.1 | 0.178 | |
| 240.0 | 0.34 | | 24.0 | 0.455 | |
| 560.0 | 0.396 | | 270.0 | 0.52 | |
| 1000.0 | 0.541 | | 1000.0 | 0.534 | |
| | | | | | |
| X-int: 3.09529 | | | X-int: 2.32803 | | |
| Y-int: -1.0753 +/- 0.20042 | | | Y-int: -0.4227 +/- 0.03448 | | |
| m: 0.34741 +/- 0.08502 | | | m: 0.18159 +/- 0.01489 | | |
| Dm: 1245.35 | | | Dm: 212.830 | | |
| r: 0.92070 | | | r: 0.99007 | | |

FIG. 10B

CI Data for Non-Constant Combo: para (cis+pac)

| Dose cis | Dose pac | Effect | CI |
|---|---|---|---|
| 1000.0 | 1000.0 | 0.54 | 0.66746 |
| 560.0 | 270.0 | 0.482 | 0.82789 |
| 240.0 | 24.0 | 0.435 | 0.68807 |
| 75.0 | 0.1 | 0.318 | 1.56946 |
| 27.0 | 0.0010 | 0.276 | 0.86127 |

CI Data for Non-Constant Combo: oppo (cis+pac)

| Dose cis | Dose pac | Effect | CI |
|---|---|---|---|
| 1000.0 | 0.0010 | 0.544 | 0.63058 |
| 560.0 | 0.1 | 0.475 | 0.88023 |
| 240.0 | 24.0 | 0.434 | 0.69977 |
| 75.0 | 270.0 | 0.395 | 7.21261 |
| 27.0 | 1000.0 | 0.486 | 0.11022 |

FIG. 10C

CI Data for Non-Constant Combo: para (cis+pac)

| Dose cis | Dose pac | Effect | CI |
|---|---|---|---|
| 1000.0 | 1000.0 | 0.579 | 1.13338 |
| 560.0 | 270.0 | 0.521 | 1.15162 |
| 240.0 | 24.0 | 0.46 | 0.57843 |
| 75.0 | 0.1 | 0.274 | 1.09571 |
| 27.0 | 0.0010 | 0.276 | 0.34901 |

CI Data for Non-Constant Combo: oppo (cis+pac)

| Dose cis | Dose pac | Effect | CI |
|---|---|---|---|
| 1000.0 | 0.0010 | 0.537 | 0.52403 |
| 560.0 | 0.1 | 0.383 | 1.78062 |
| 240.0 | 24.0 | 0.48 | 0.41788 |
| 75.0 | 270.0 | 0.491 | 1.61362 |
| 27.0 | 1000.0 | 0.503 | 4.41907 |

FIG. 10D

SYSTEM AND METHOD FOR SCREENING THERAPEUTIC AGENTS

CROSS REFERENCE TO RELATED APPLICATIONS

This application claims the benefit of U.S. Provisional Patent Application No. 63/027,397, filed May 20, 2020, which is incorporated herein by reference in its entirety.

STATEMENT REGARDING FEDERAL FUNDING

This invention was made with United States government support under CA047904 and AG061005 awarded by the National Institutes of Health; FA9550-18-1-0262 awarded by the U.S. Air Force; and N000141712566 awarded by the Office of Naval Research. The U.S. government has certain rights in the invention.

Provided herein are devices useful for screening therapeutic agents for efficacy. Also provided herein are methods of screening therapeutic agents for efficacy.

Advancements in drug screening build off a substantial body of work with ex vivo cell culture models on 2D systems. These approaches are powerful, as they often resemble physiologically relevant environments. Therefore, building 3D microenvironments that better mimic in vivo conditions has been of great interest. Part of these advances is the development of microfluidic systems representative of vasculature. Advancements in drug circulatory diffusion have been developed with microfluidic systems to replicate the surrounding tumor vasculature. Polydimethylsiloxane (PDMS) is often used as a primary material for microfluidic chip fabrication due to its flexibility and high gas permeability. However, PDMS does not form a biocompatible extracellular matrix for 3D cell culture, but rather serves as an inorganic substrate that lacks physiological features of normal tissue. In addition, PDMS has a strong hydrophobic nature that causes hydrogen bonding or polar-polar interactions negatively influencing drug diffusion.

Collagen makes up approximately 30% of the protein in the body, while PDMS does not exist in the body. Thus, combining microfluidic collagen-embedded channels with techniques such as sacrificial template molding and 3D bioprinting closes the gap between ex vivo cell culture models and animal models. Clearly, animal models provide much greater physiological relevance, but are less cost effective and can yield responses which are relevant to animals but are unintentionally misleading in humans. Importantly, animal models often lack immune system functionality and species-specific drug response, thus, presenting inconsistent responses compared to clinical trials in human patients. Besides, animal models are less controllable in experimental manipulation during tumor progression, and randomness of tumor invasion in animal models increases difficulty in real-time imaging. These limitations lead to the needs of a more flexible, controllable, and high-throughput model for tumor study.

Several tumor-on-a-chip models have been developed in recent years to overcome limitations of existing techniques, however, an effective system for modeling the tumor environment in a patient is desirable.

SUMMARY

In one aspect or embodiment, a device is provided comprising: a containment structure; a biocompatible hydrogel contained within the containment structure, comprising a first well configured to retain a liquid within the hydrogel; and a live, solid tissue sample embedded in the hydrogel and spaced apart from the first well.

In another aspect or embodiment, a method of making a device for use in analyzing safety and efficacy of one or more therapeutic agents is provided. The method comprises: placing a live, solid tissue sample in a containment structure; and forming over the tissue sample in the containment structure, a biocompatible hydrogel having a first well configured to retain a liquid in the hydrogel.

In another aspect or embodiment, a method of determining a therapeutically-effective dosage of a therapeutic agent, comprising: placing a sample of the therapeutic agent in a well of a device comprising: a containment structure; a biocompatible hydrogel contained within the containment structure, comprising a first well configured to retain a liquid within the hydrogel; and a live tissue sample or samples embedded in the hydrogel and spaced apart from the first well; incubating the device at a suitable incubation temperature for the tissue sample or samples for a time period sufficient to establish a concentration gradient of the drug in the hydrogel; determining or measuring, for two or more positions in the hydrogel of the device containing the tissue sample or samples, the drug dosage at the end of the time period; determining the effect of the drug on the tissue sample at the two or more positions; and determining an effective dose of the drug based on the determination of the effect of the drug on the tissue sample at the two or more positions.

The following numbered clauses describe various aspects or embodiments of the invention.

Clause 1. A device comprising:
a containment structure;
a biocompatible hydrogel contained within the containment structure, comprising a first well configured to retain a liquid within the hydrogel; and
a live, solid tissue sample embedded in the hydrogel and spaced apart from the first well.

Clause 2. The device of clause 1, wherein the tissue sample is a contiguous tissue sample comprising a first portion and a second portion, that is arranged within the hydrogel so that the first portion is a first distance from the well, and the second portion is a second distance from the well that is greater than, e.g., at least 10% greater than, the first distance from the well.

Clause 3. The device of clause 1, comprising two or more tissue samples spaced at different distances from the first well.

Clause 4. The device of any one of clauses 1-3, wherein the hydrogel comprises a second well that is spaced-apart from the first well.

Clause 5. The device of clause 4, wherein the second well is a larger distance from the first well than from any of the two or more tissue samples.

Clause 6. The device of clause 4, wherein the two or more tissue samples are between the first well and the second well.

Clause 7. The device of any one of clauses 3-6, wherein the two or more tissue samples are arranged substantially linearly.

Clause 8. The device of any one of clauses 1-7 wherein the hydrogel comprises at least three wells spaced around the tissue sample or samples.

Clause 9. The device of any one of clauses 1-8, wherein at least one of the wells is elongated.

Clause 10. The device of clause 9, wherein the wells are slots or channels arranged about a circumference of the tissue sample or samples.

Clause 11. The device of any one of clauses 1-10, comprising a therapeutic agent in one or more of the wells, wherein the therapeutic agent is optionally a drug, such as a chemotherapeutic drug.

Clause 12. The device of any one of clauses 1-11, configured as a cartridge for use in an automated system for incubating and/or analyzing the tissue sample.

Clause 13. The device of any one of clauses 1-12, wherein at least one of the wells comprises a channel embedded within the hydrogel having outlets extending to a surface of the hydrogel.

Clause 14. The device of any one of clauses 1-13, wherein the tissue sample is a biopsy obtained from a human or veterinary patient.

Clause 15. The device of any one of clauses 1-14, wherein the tissue sample is a sample of an abnormal tissue mass.

Clause 16. The device of any one of clauses 1-15, wherein the hydrogel comprises an extracellular matrix material.

Clause 17. The device of clause 16, wherein the hydrogel is a collagen hydrogel.

Clause 18. A method of making a device for use in analyzing safety and efficacy of one or more therapeutic agents, comprising:

placing a live, solid tissue sample in a containment structure; and forming over the tissue sample in the containment structure, a biocompatible hydrogel having a first well configured to retain a liquid in the hydrogel.

Clause 19. The method of clause 18, wherein the tissue sample is a contiguous tissue sample comprising a first portion and a second portion, that is arranged within the hydrogel so that the first portion is a first distance from the well, and the second portion is a second distance from the well that is greater than, e.g., at least 10% greater than, the first distance from the well.

Clause 20. The method of clause 18, wherein two or more tissue samples are spaced at different distances from the first well.

Clause 21. The method of any one of clauses 18-20, further comprising forming a second well that is spaced-apart from the first well.

Clause 22. The method of clause 21, wherein the second well is formed a larger distance from the first well than from any of the two or more tissue samples.

Clause 23. The method of clause 21, wherein the two or more tissue samples are placed between the first well and the second well.

Clause 24. The method of any one of clauses 20-23, wherein the two or more tissue samples are arranged substantially linearly.

Clause 25. The method of any one of clauses 18-24, comprising forming at least three wells spaced around the tissue sample or samples.

Clause 26. The method of any one of clauses 18-25, wherein at least one of the wells is elongated.

Clause 27. The method of clause 26, wherein the wells are slots or channels arranged about a circumference of the tissue sample or samples.

Clause 28. The method of any one of clauses 18-27, wherein the containment structure is configured as a cartridge for use in an automated system for incubating and/or analyzing the tissue sample.

Clause 29. The method of any one of clauses 18-28, wherein at least one of the wells is formed as a channel embedded within the hydrogel having outlets extending to a surface of the hydrogel.

Clause 30. The method of any one of clauses 18-29, wherein the tissue sample is a biopsy obtained from a human or veterinary patient.

Clause 31. The method of any one of clauses 18-30, wherein the tissue sample is a sample of an abnormal tissue mass.

Clause 32. The method of any one of clauses 18-31, wherein the containment structure comprises a mold element defining the well or wells, wherein optionally the mold element is gelatin.

Clause 33. A method of determining a therapeutically-effective dosage of a therapeutic agent, comprising:

placing a sample of the therapeutic agent in a well of a device comprising:

a containment structure;

a biocompatible hydrogel contained within the containment structure, comprising a first well configured to retain a liquid within the hydrogel; and a live tissue sample or samples embedded in the hydrogel and spaced apart from the first well;

incubating the device at a suitable incubation temperature for the tissue sample or samples for a time period sufficient to establish a concentration gradient of the therapeutic agent in the hydrogel;

determining or measuring, for two or more positions in the hydrogel of the device containing the tissue sample or samples, the therapeutic agent dosage at the end of the time period;

determining the effect of the therapeutic agent on the tissue sample at the two or more positions; and determining an effective dose of the therapeutic agent based on the determination of the effect of the therapeutic agent on the tissue sample at the two or more positions, wherein the therapeutic agent is optionally a drug, such as a chemotherapeutic drug.

Clause 34. The method of clause 33, wherein the concentration of the therapeutic agent at the end of the time period is used as a measure of the therapeutic agent dosage at the two or more positions.

Clause 35. The method of clause 33, wherein determining the effect of the therapeutic agent on the tissue sample, comprises quantifying cell viability at the end of the time period for tissue samples at the two or more positions.

Clause 36. The method of clause 33 or 34, wherein determining the effect of the therapeutic agent on the tissue sample at the two or more positions, includes performing on tissue samples at each of the two or more positions live/dead staining assay, a cell proliferation assay, and/or a cell apoptosis assay.

Clause 37. The method of any one of clauses 33-36, wherein the cell proliferation assay determines Ki-67 expression, and the apoptosis assay determines caspase 3 expression.

Clause 38. The method of any one of clauses 33-37, wherein the tissue sample is a contiguous tissue sample comprising a first portion and a second portion, that is arranged within the hydrogel so that the first portion is a first distance from the well, and the second portion is a second distance from the well that is greater than, e.g., at least 10% greater than, the first distance from the well.

Clause 39. The method of any one of clauses 33-37, wherein the device comprises two or more tissue samples spaced at different distances from the first well.

Clause 40. The method of any one of clauses 33-39, wherein the hydrogel further comprises a second well that is spaced-apart from the first well.

Clause 41. The method of clause 40, wherein the second well is a larger distance from the first well than from any of the two or more tissue samples.

Clause 42. The method of clause 40, wherein the two or more tissue samples are between the first well and the second well.

Clause 43. The method of clause 40, wherein the two or more tissue samples are arranged substantially linearly.

Clause 44. The method of any one of clauses 33-39, wherein the hydrogel comprises at least three wells spaced around the tissue sample or samples.

Clause 45. The method of any one of clauses 33-44, wherein at least one of the wells is elongated.

Clause 46. The method of clause 45, wherein the wells are slots or channels arranged about a circumference of the tissue sample or samples.

Clause 47. The method of any one of clauses 33-46, wherein at least one of the wells comprises a channel embedded within the hydrogel having outlets extending to a surface of the hydrogel.

Clause 48. The method of any one of clauses 33-47, wherein the tissue sample is a solid tissue, such as a biopsy obtained from a human or veterinary patient.

Clause 49. The method of any one of clauses 33-47, wherein the tissue sample is a sample of an abnormal tissue mass.

Clause 50. The method of any one of clauses 33-49, wherein the hydrogel comprises collagen.

Clause 51. The method of clause 50, wherein the hydrogel is a collagen hydrogel.

Clause 52. The method of any one of clauses 40-51, wherein a first therapeutic agent is placed in, and diffuses from the first well, and a second therapeutic agent is placed in, and diffuses from one or more different wells, and the therapeutic agent dosage for each therapeutic agent is determined or measured for each of the two or more positions in the hydrogel of the device at the end of the time period.

Clause 53. The method of clause 52, further comprising quantifying cell viability at the end of the time period for tissue samples at each of the two or more positions and determining a Combination Index (CI) for the therapeutic agent combination from the quantification of cell viability.

Clause 54. The method of any one of clauses 33-53, wherein the tissue sample or samples are from a tumor biopsy of a patient, and the method further comprising treating the patient with a dosage regimen of effective amounts of one or more therapeutic agents based on the determination of an effective dose of the one or more therapeutic agents based on the determination of the effect of the one or more therapeutic agents on the tissue sample at the two or more positions.

Clause 55. The method of any one of clauses 33-54, wherein the therapeutic agent is a chemotherapeutic agent, and the tissue sample is tumor tissue obtained from the patient.

Figure 1A:
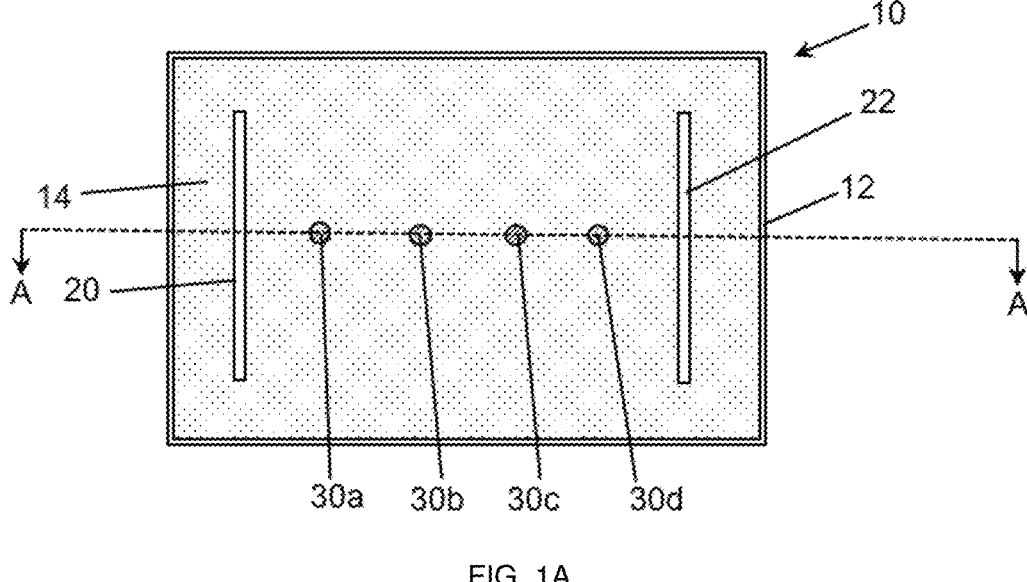
FIGS. 1A-1D provide examples of a device described herein, with FIG. 1A providing a top view of a device having
Figure 1B:
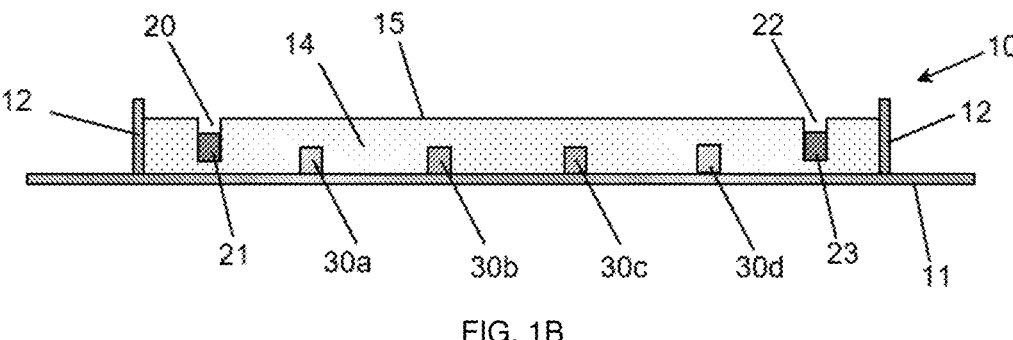
Figure 1C:
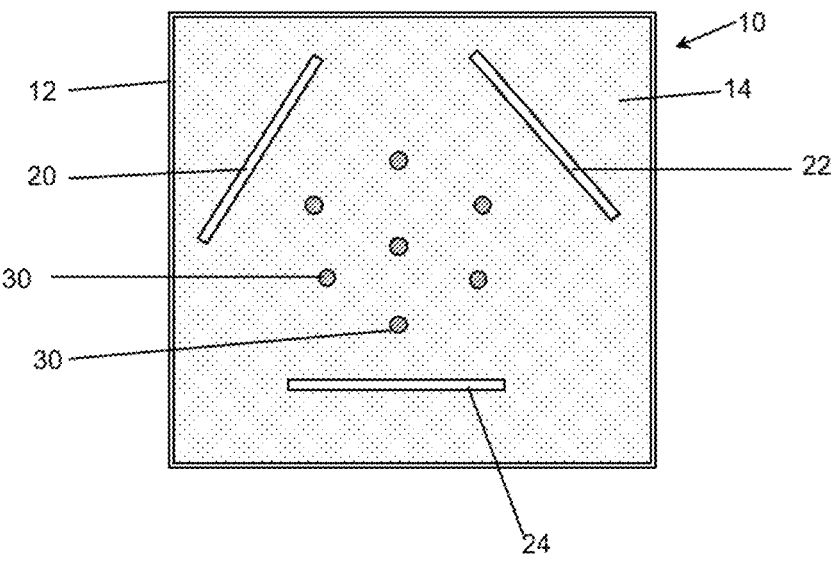

6 two wells, with FIG. 1B showing a side cross sectional view of the device of FIG. 1A at "A"; FIG. 1C providing a top view of a device having three wells; and FIG. 1D providing a top view of a device having four wells.

Figure 2A:
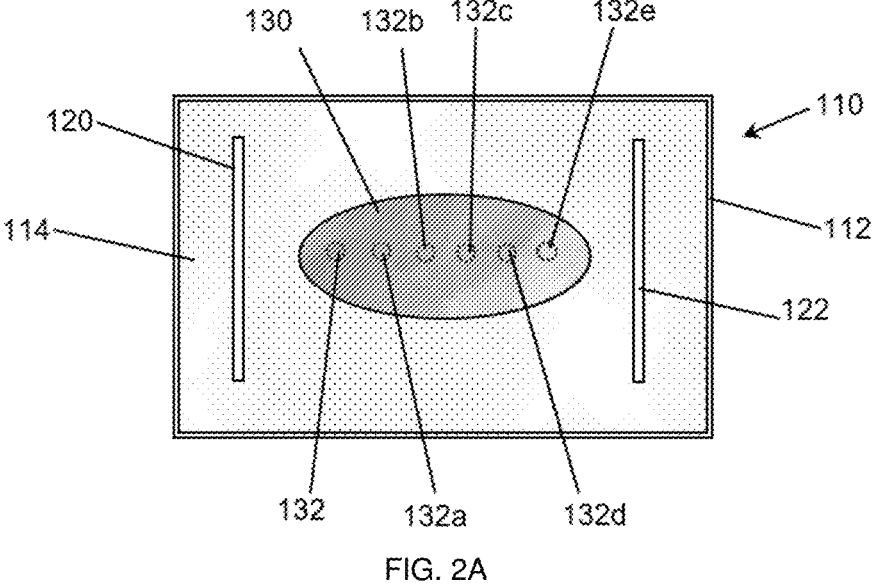
Figure 2B:
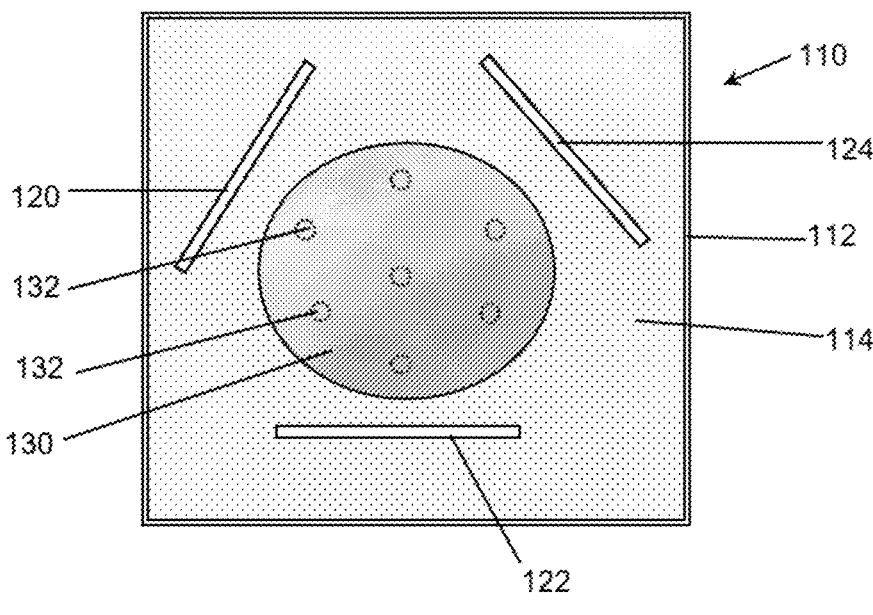

FIGS. 2A and 2B provide top views of examples of two-well (FIG. 2A) and three-well (FIG. 2B) devices as described herein using a larger solid tissue sample.

Figure 3A:
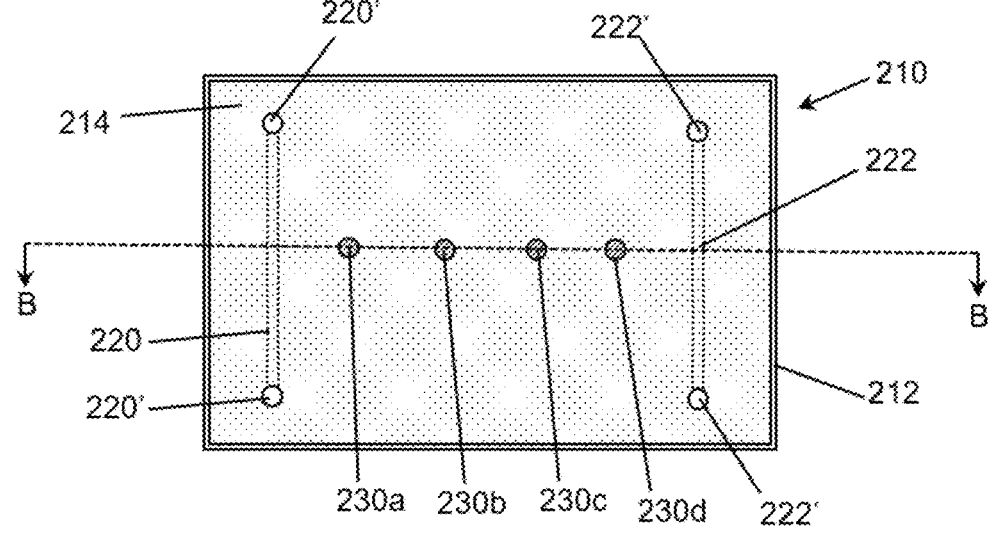
Figure 3B:
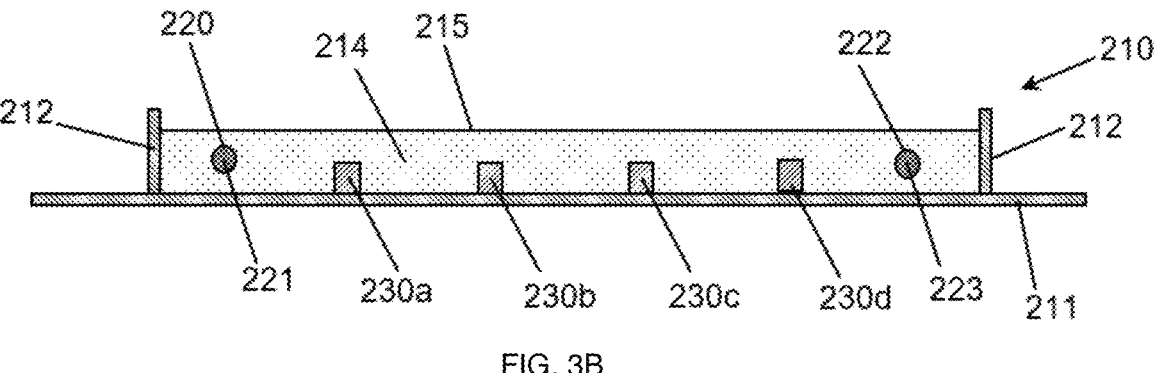

FIGS. 3A and 3B provide a top-view (FIG. 3A) and a cross-sectional side view (FIG. 3B) at "B" in reference to FIG. 3A, of a device having two wells configured as channels.

FIG. 4 provides exemplary Matlab code for simulating and predicted the diffusion profile of drugs as described in the Examples.

FIG. 5. 3D Collagen vascular tumor-on-a-chip mimetics for dynamic combinatorial drug screening. A. A microfluidic 3D extracellular matrix (ECM) based drug screening device could fill the gap between ex vivo models and animal models, with more physiological relevance compared to ex vivo models, and more direct controllability than animal models. B. Design of a 3D ECM based dynamic tumor-on-a-chip drug screening device. Tumors were positioned between two parallel channels. Microfluidic channels on both ends were available for drug perfusion. The 3D dynamic diffusion approach (left) was designed to mimic in vivo drug delivery from blood vessels to tumors (right). Drug molecules were perfused into ECM embedded microfluidic channels, and then the molecules physically diffused into ECM, generating a drug gradient in the scaffold.

Figure 6B:
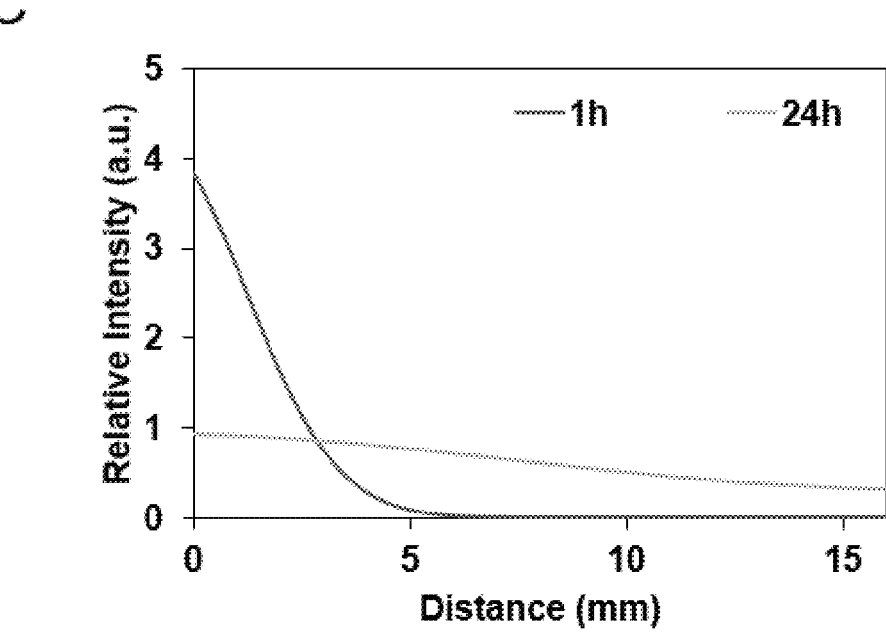
Figure 6C:
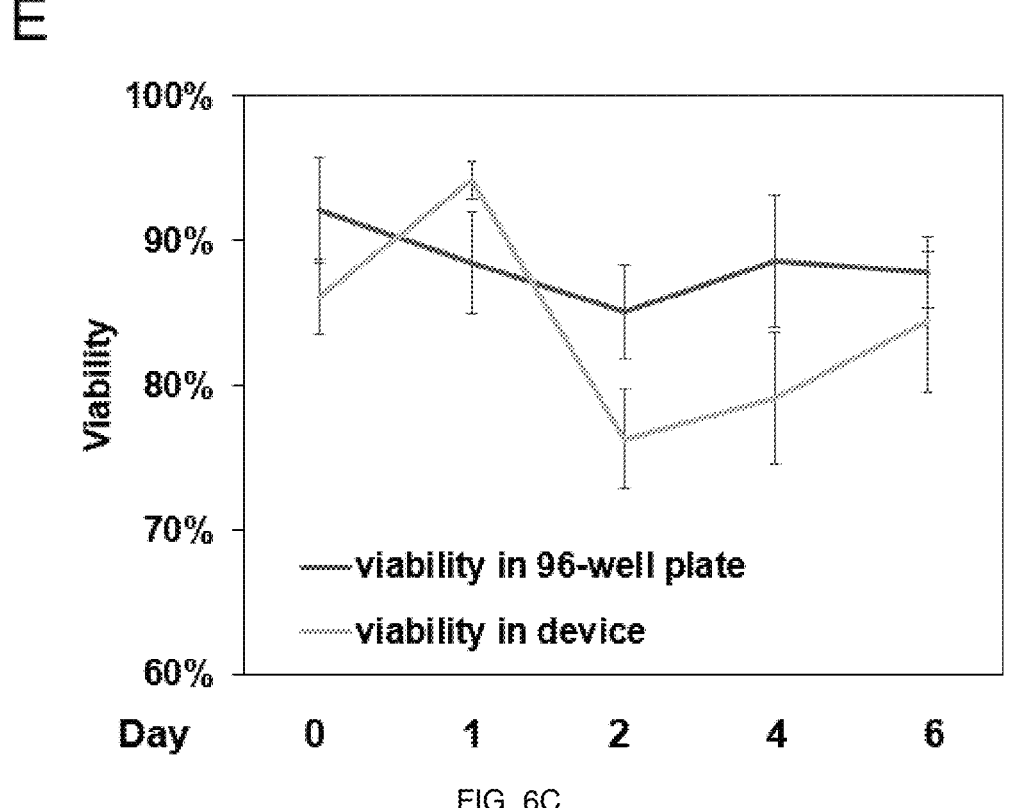

FIGS. 6A-6C. Diffusion profiles and cell viability in our ECM based systems. FIG. 6A. A doxorubicin diffusion profile was captured through confocal microscopy imaging of doxorubicin fluorescent intensity at 1 and 24 h. FIG. 6A. Quantification of doxorubicin diffusion for 1 and 24 h. The grey line was the baseline fluorescence intensity without the presence of doxorubicin. FIG. 6B. 1D simulation of doxorubicin diffusion profile generated by applying the diffusion coefficient of doxorubicin from literature data. The simulation was similar to experimental results for the 1 and 24 h diffusion profiles. FIG. 6B. Viability tests for tumor samples cultured in 96-well plates and in our ECM tumor-on-a-chip device. FIG. 6C. Live/dead staining of tumor samples from Day 0 to Day 6, in 96-well plates and in our device. Scale bar: 200 µm.

Figure 7A:
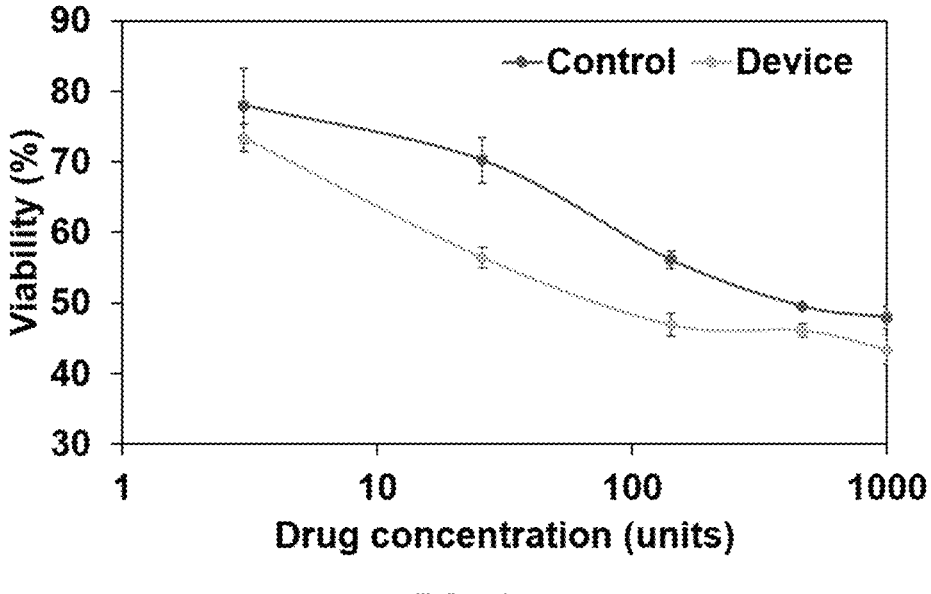
Figure 7B:
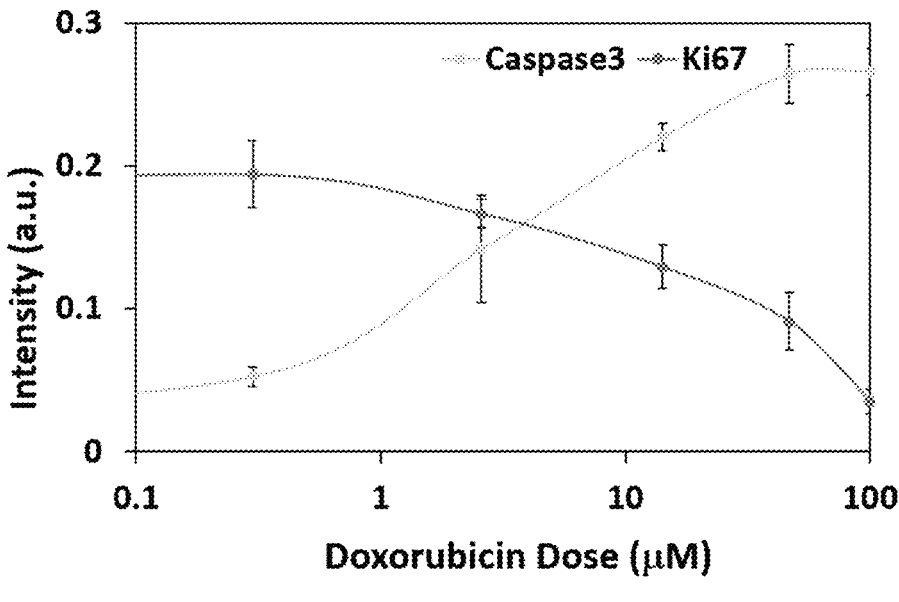

FIGS. 7A and 7B. Tumor-on-a-chip response to single drug exposure. 3D devices vs. 2D controls setup. Top: Five tumors were inserted in series into the system. Middle: Simulation of drug diffusion profile for 24, 48, and 72 h. Bottom: In a 2D control, tumors were cultured in 96-well plates and treated directly with constant drug doses equal to the drug dose in the 3D device at 48 h. FIG. 7A. Doxorubicin drug screening results for the device and control. Note that both presented similar trends, yet the absolute drug effect was different. For doxorubicin, 1000 units=100 µM. Experiments were done in triplicates. Immunofluorescent staining for DAPI, Ki-67, and caspase 3, and autofluorescence of doxorubicin, in tumor samples treated with doxorubicin showed that expression of caspase 3 increased and Ki-67 decreased with higher dosing, which agreed with the live/dead staining results. FIG. 7B. Quantification of immunofluorescent staining intensity of caspase 3 and Ki-67. The lines are polynomial interpolations.

FIGS. 8A-8C. Double drug screening with doxorubicin (doxo) and cyclophosphamide (cyclo). A. COMPUSYN analysis of 2D 96 well-plate control. B. COMPUSYN analysis of 3D ECM microsystem. C. Drug screening results for cyclo & doxo in para dosing in 2D control. The diamond and square marker curves indicate single drug treatments, and the triangle marker curves indicate parallel direction drug combination results. Combination index values are labeled at each data point. D. Drug screening results for cyclo & doxo in para dosing in 3D ECM microsystem. E. Drug screening results for cyclo & doxo in oppo dosing in 2D control. The diamond and square marker curves indicate single drug treatments, and the triangle marker curve indicates opposite directions. F. Drug screening results for cyclo & doxo in oppo dosing in 3D ECM microsystem. Experiments were done in triplicates.

Figure 9:

FIG. 9. COMPUSYN Interpolation for single drug dose-effect curve and median-effect curve in (A) control and (B) device. Dose: drug dose applied. For doxorubicin, 1000 units=100 μM. For cyclophosphamide, 1000 units=100 mM. Effect: the drug effect equals the death rate. M: the dynamic order equals the slope of the median-effect plot. Dm: the median-effect dose. R: the linear correlation coefficient of the median-effect plot. Fa/Fu: the fraction of cells affected (death) and fraction unaffected. D: the dose applied in experiment.

Figures 10E, 10F:
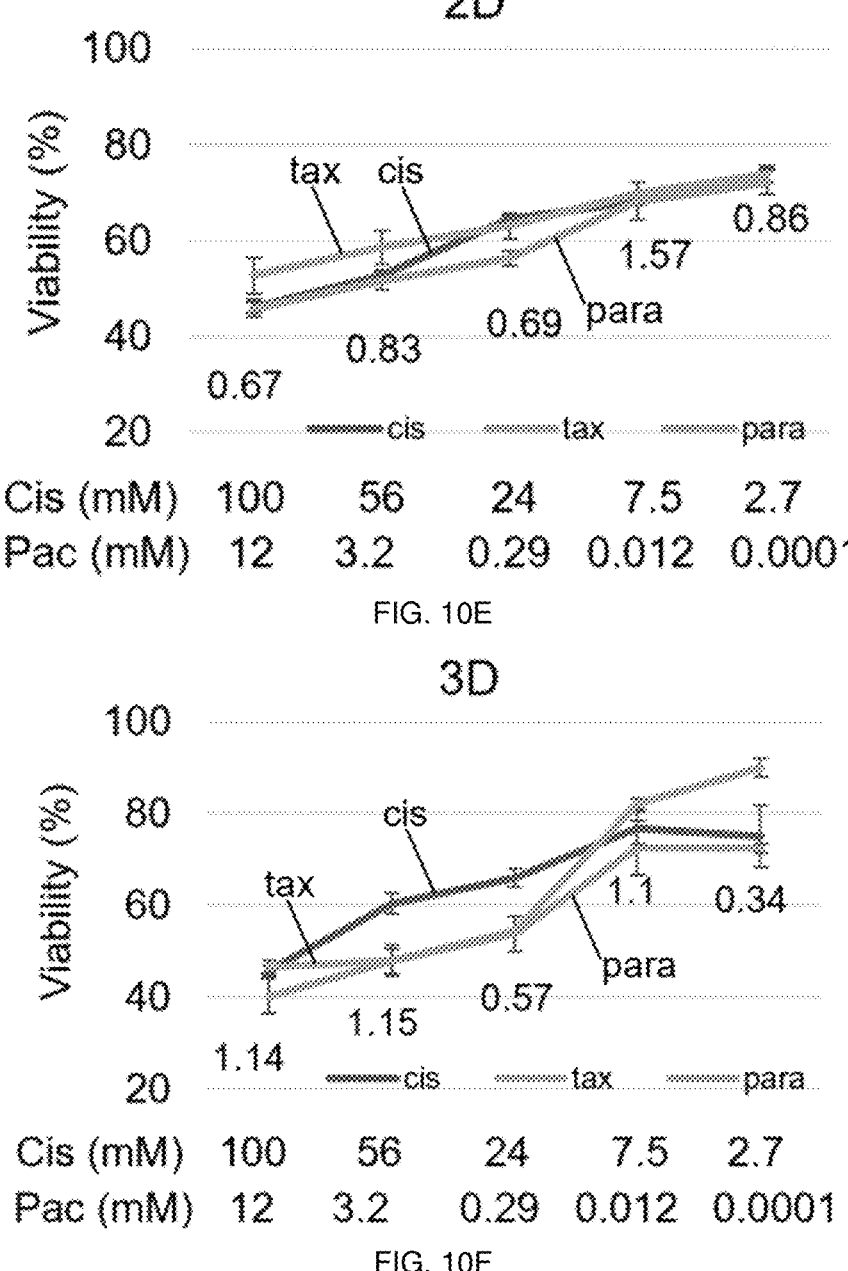
Figure 10G:
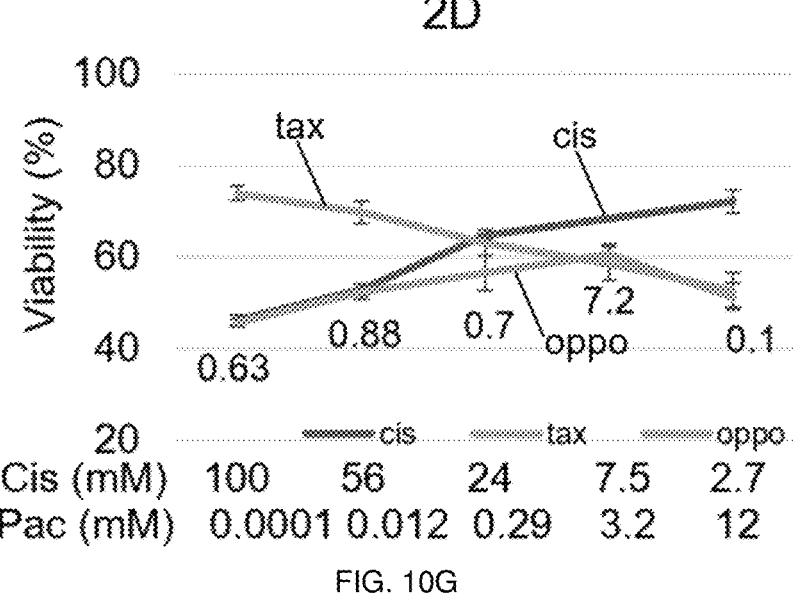
Figure 10H:
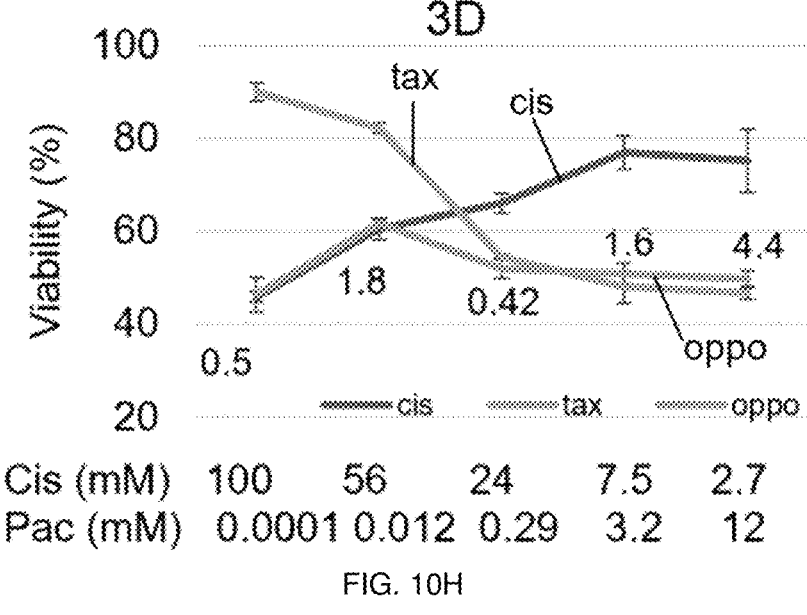

FIGS. 10A-10H. COMPUSYN Interpolation for single drug dose-effect curve and median-effect curve in (FIG. 10A) control and (FIG. 10B) device. Dose: drug dose applied. For cisplatin, 1000 units=100 μM. For paclitaxel, 1000 units=12 μM. Effect: the drug effect, equals to the death rate. M: the dynamic order equals the slope of the median-effect plot. Dm: the median-effect dose. R: the linear correlation coefficient of the median-effect plot. Fa/Fu: the fraction of cells affected (killed) and the fraction unaffected. D: dose applied in experiment. Combination index value for each individual combination data point in cis & pac drug combination, for control (FIG. 10C) and device (FIG. 10D). FIG. 10E. Drug screening results for cis & pac in para dosing in 2D 96 well plate control. The cis and pax curves indicate single drug treatments, and the para curves indicate parallel direction drug combination results. Combination index values are labeled at each data point. FIG. 10F. Drug screening results for cis & pac in para dosing in 3D ECM microsystem. FIG. 10G. Drug screening results for cis & pac in oppo dosing in 2D control. FIG. 10H Drug screening results for cis & pac in oppo dosing in 3D ECM microsystem.

Figures 11A, 11B:
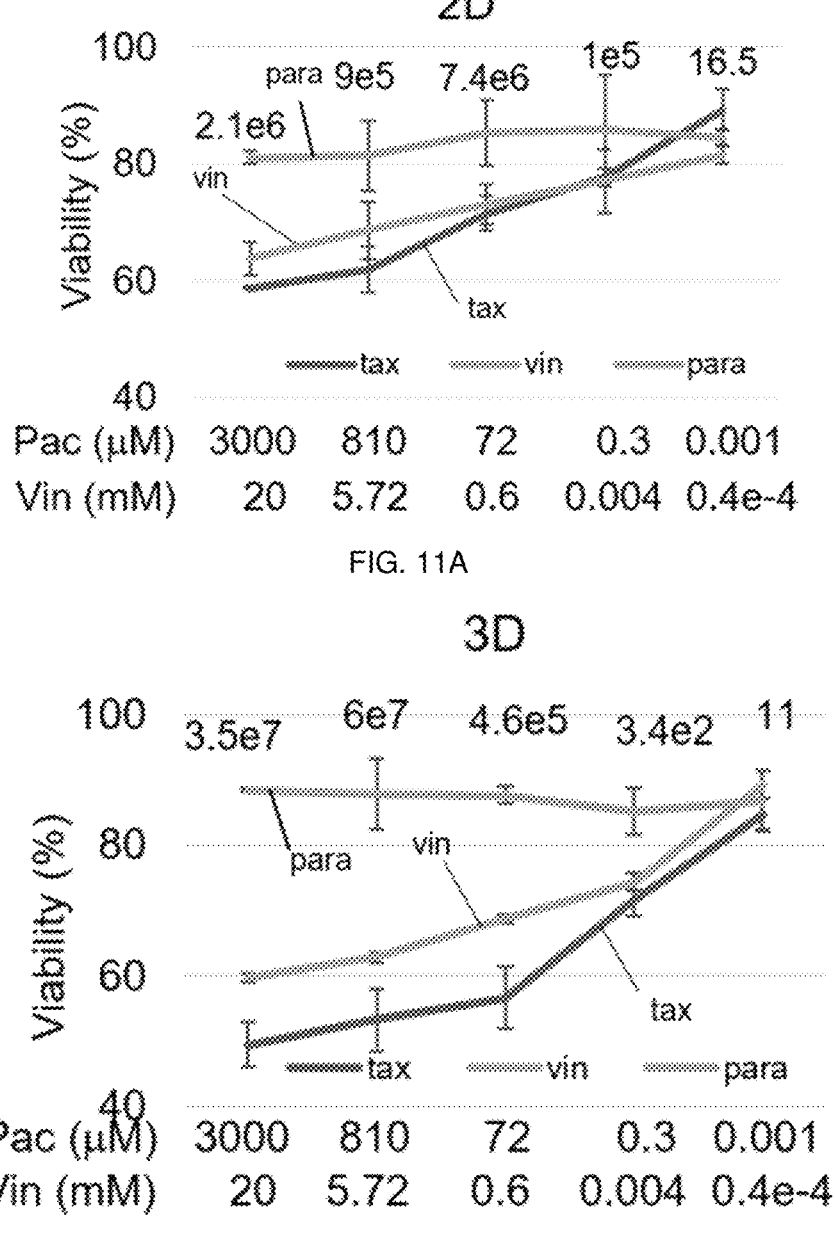
Figure 11C:
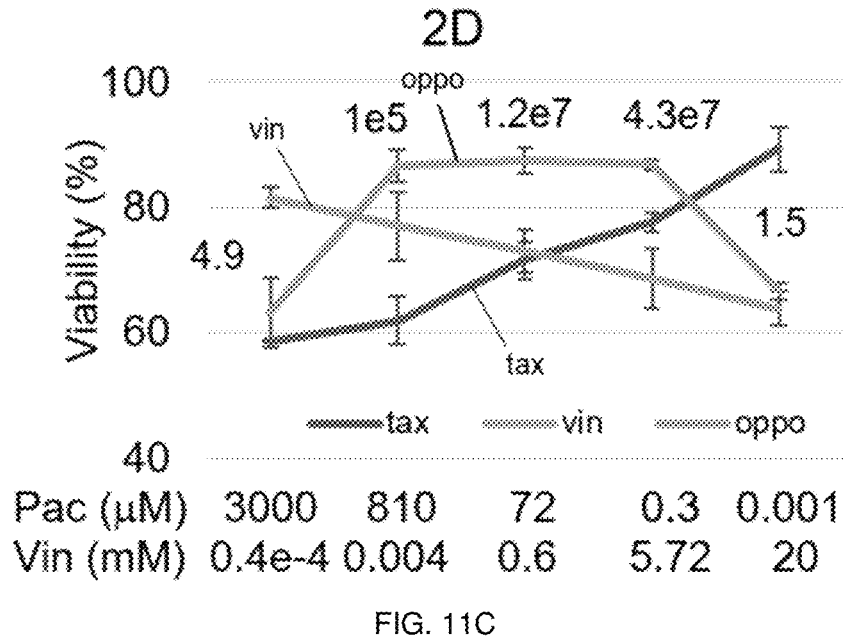
Figure 11D:
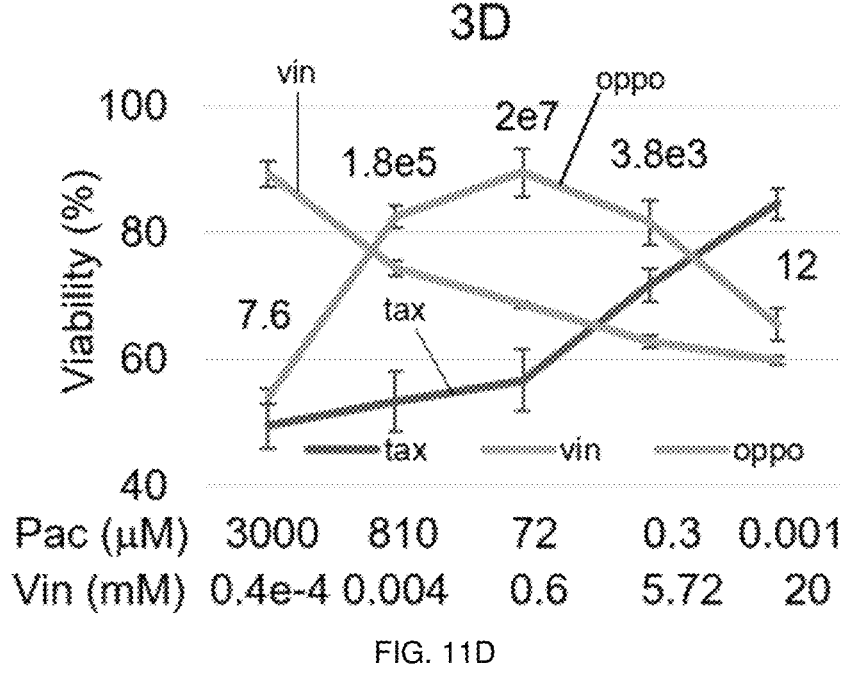
Figure 11E:
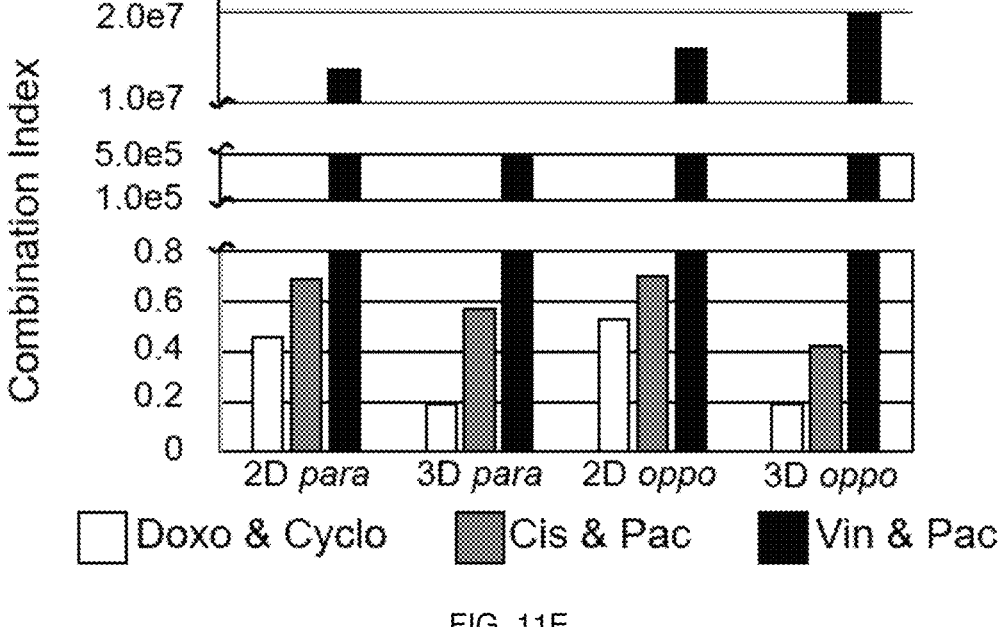

FIGS. 11A-11E. Comparison of a known antagonistic drug interaction in 2D and the 3D ECM microsystem. FIG. 11A. Drug screening results of paclitaxel (pac) and vincristine (yin) in para dosing in 2D 96 well plate control. The pac and yin curves indicate single drug treatments, and the para curves indicate parallel direction drug combination results. Combination index (CI) values are labeled at each data point. FIG. 11B. Drug screening results for pac & yin in para dosing in 3D ECM microsystem. FIG. 11C. Drug screening results for pac & yin in oppo dosing in 2D control. FIG. 11D. Drug screening results for pac & yin in oppo dosing in 3D ECM microsystem. FIG. 11E. CI comparison between all 3 drug combinations (doxo & cyclo, cis & pac, and pac & yin) at double-median dosing.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

The present invention will be described, in part, with reference to the accompanying drawings where like reference numbers correspond to like elements.

For purposes of the description hereinafter, spatial or directional terms shall relate to the invention as it is oriented in the drawing figures. However, it is to be understood that the invention may assume various alternative variations, except where expressly specified to the contrary. It is also to be understood that the specific components illustrated in the attached drawings, and described in the following specification, are simply exemplary embodiments of the invention.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings and "mammal" refers to all mammals, including, but not limited to human beings.

As used herein, the "treatment" or "treating" of a patient means administration to a patient by any suitable dosage regimen, procedure and/or administration route of a composition, device or structure with the object of achieving a desirable clinical/medical end-point, including administration of effective amounts of a drug composition, and killing cancer cells or reducing tumor size.

As used herein, the term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas co-polymers contain more than one type of monomer. A biological polymer is a naturally-occurring polymer that can be found in a living organism, even though it may be synthesized by man, for example by recombinant means, by de-novo synthesis, etc. As an example, collagen is a biological polymer, even though it may be manufactured by procession of tissue or by other methods, and includes proteins or peptides having a natural (found in nature) collagen sequence, whether or not co- or post-translationally modified, or in the form of procollagen or mature collagen. A synthetic polymer is a polymer that does not occur in nature.

A polymer "comprises" or is "derived from" a stated monomer if that monomer is incorporated into the polymer. Thus, the incorporated monomer (e.g., "residue") that the polymer comprises is not the same as the monomer prior to incorporation into a polymer, in that at the very least, certain linking groups are introduced and/or are incorporated into the polymer backbone or certain moieties of the monomer are removed in the polymerization process. A polymer is said to comprise a specific type of linkage if that linkage is present in the polymer.

Provided herein are devices for use in screening drugs for safety and efficacy in treating a disease, such as a hyperplasia, e.g., a cancer. Also provided herein are methods of treating a patient using the devices, and methods of screening drugs for safety and efficacy in treating a disease, such as a hyperplasia, e.g., a cancer. Multi-drug synergy or antagonism may be readily ascertained using the devices and methods described herein.

FIGS. 1A-1D and 2A-2B depict schematically various embodiments of devices described herein. FIG. 1A depicts schematically a top view of an exemplary device 10 as described herein. FIG. 1B is a cross-sectional view of the device 10 depicted in FIG. 1A. In reference to FIGS. 1A and 1B, device 10, comprises a substrate 11, such as a glass slide, and a wall 12, containing a hydrogel 14 having a top surface 15. The substrate 11 and wall 12 define a chamber in which the hydrogel is contained, and the chamber may be open as depicted or closed, comprising a partial or full lid (not shown). Two elongated wells 20 and 22 are formed within the hydrogel, as described herein. Solid tissue samples 30a-30d are embedded in the hydrogel 14. Depicted in FIG. 1B is a first drug sample 21 in well 20, and a second drug sample 23 in well 22. In use, a first drug contained in the first drug sample 21 diffuses in a direction from sample 30a to 30d. With tissue samples 30a-30d each being spaced, respectively, a larger distance from well 20, a concentration gradient of the drug of the first drug sample 21 may be produced. Likewise, a second drug contained in the second drug sample 23 diffuses in a direction from tissue samples 30d to 30a. With tissue samples 30d-30a each being spaced, respectively, a larger distance from well 22, a concentration gradient of the drug of the second drug sample 23 may be produced. The drug concentration or dosage (e.g., AUC) over time at the location of any given sample may be determined by any useful method, such as by the methods described in the examples, below. It should be noted that more than one drug, or no drug, may be contained, independently in any drug sample used in the devices exemplified in FIGS. 1A-1D and 2A-2B. Further, a drug in any drug sample may be dosed into each well according to any dosing profile, including as a single bolus, continuously, or in multiple doses spaced out over time.

It is further noted, that in FIG. 1A, and elsewhere herein, the arrangement of tissue samples 30a through 30d is depicted as linear and perpendicular to the long (largest) dimension of the elongated well 20 and to the long dimension of parallel well 22. Other arrangements of the wells 20 and 22, and tissue samples 30a-30d may be employed to substantially equal effect, and determination of concentration and drug dose for any tissue sample, also may be readily determined. By "elongate" or "elongated" in reference to wells, it is meant that, the well has a depth from a top, exposed surface 15 of the hydrogel 14, and a width and length measured substantially in the plane of the surface 15 of the hydrogel 14, with, in reference to FIG. 1A, the width being the left-to-right dimension, and the length being the top-to bottom dimension, with the length being longer than the width, such as 2 times (2×), 3×, 4×, 5×, 6×, 7×, 8×, 9×, or 10×, the dimension of the width, or more, in essentially a linear configuration, as depicted in FIG. 1A. As shown in FIG. 1A, the elongate wells 20 and 22 may be arranged in parallel, with the tissue samples 30a-30d between the wells 20 and 22. The elongated wells may be described as being arranged about a circumference of the tissue sample(s) because they surround the tissue sample(s).

Figure 1D:
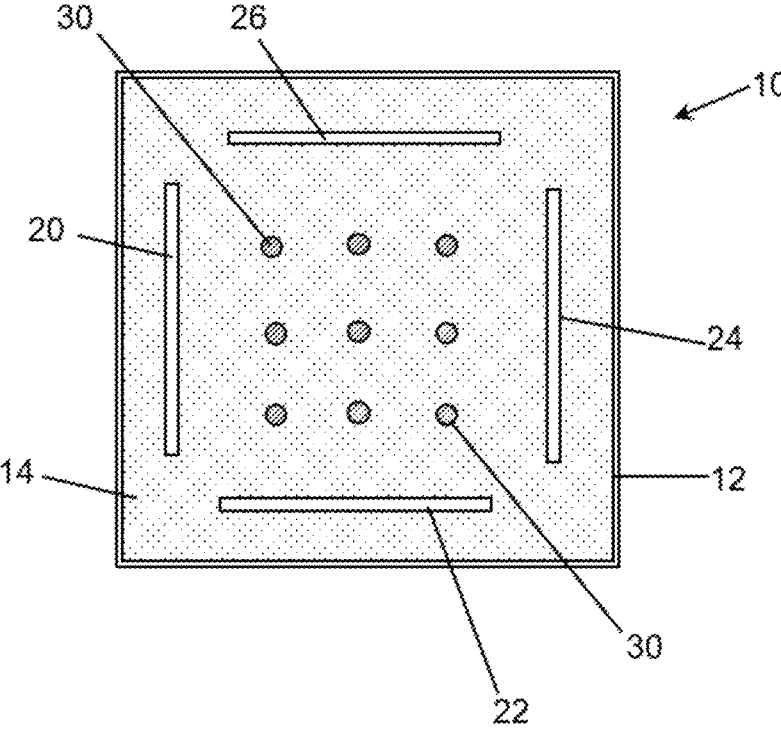

Referring to FIGS. 1C and 1D, the device may have three wells (FIG. 1C), or four wells (FIG. 1D). Devices shown in FIGS. 1C and 1D, are depicted in top view only. In FIGS. 1C and 1D, the device 10, a wall 12, containing a hydrogel 14, essentially as depicted in FIGS. 1A and 1B. In FIG. 1C, three elongated wells 20, 22, and 24 are formed within the hydrogel 14, as described herein. In FIG. 1D, four elongated wells 20, 22, 24, and 26 are formed within the hydrogel 14, as described herein. In both of FIGS. 1C and 1D, solid tissue samples 30 are embedded in the hydrogel 14. The arrangement of the wells 20, 22, 24, and 26 and tissue samples 30 in FIGS. 1C and 1D, and as with FIGS. 1A and 1B, any effective arrangement may be used. In FIGS. 1C and 1D, up to four different drug sample may be tested, with different drugs deposited in each of wells 20, 22, 24, and 26, and their concentration or dosage at each tissue sample 30 being determinable as described herein. Additional wells (five or more) may be fabricated into the hydrogel as described.

Referring to FIGS. 2A and 2B, instead of multiple tissue samples, if available from a patient having, e.g., a tumor of sufficient size, a single solid tissue sample, such as a slice of a tumor, may be used. The devices 110 depicted in FIGS. 2A and 2B, comprise a wall 112, a hydrogel 114, and wells 120, 122, and 124, with two wells being depicted in FIG. 2A, and three wells being depicted in FIG. 2B. A single solid tissue sample 130 is depicted, and positions 132a-132e are depicted in relation to the tissue sample 130. Referring to FIG. 2A, as with individual tissue samples 30a-30b in FIGS. 1A and 1B, drug from well 120 will diffuse in a direction of position 132a to position 132e, and drug from well 122 will diffuse in a direction from position 132e to position 132a, and concentration or dosage at each position 132a-132e, being determinable as described herein. Different numbers of positions than those depicted in FIGS. 2A and 2B may be used to determine optimal drug and dosage effect.

Tissue samples may be placed in the device described herein at any useful location, or positions (e.g., positions in reference to FIGS. 2A and 2B) in a single or multiple tissue samples, and may be pre-defined, to provide at least two, and preferably more, positions in which different drug concentrations or amounts can be produced over the assay. In reference to FIGS. 2A and 2B, in defining different positions to determine dosage effect, the positions (e.g., 132a-132e) may be predetermined, where the tissue samples may be placed in pre-determined and in some instances marked locations in the device. Alternatively, given the wide variety of imaging devices available, the location of the tissue sample(s) within the device may be imaged, and the drug concentration or dose at each tissue sample or positions on a single, or multiple larger samples embedded in the hydrogel may be modeled, for example as shown below, based on factors affecting diffusion in the hydrogel.

In an alternative to the channel-like wells as shown in FIGS. 1A and 1B, tubular wells or channel may be used to deliver the drug samples. In reference to FIGS. 3A and 3B, device 210, may comprise a substrate 211, such as a glass slide, and a wall 212, containing a hydrogel 214 having a top surface 215. Two tubular wells 220 and 222 are formed or embedded as channels within the hydrogel, as described herein. Solid tissue samples 230a-230d are embedded in the hydrogel 14. Depicted in FIG. 3B is a first drug sample 221 in well 220, and a second drug sample 223 in well 222. The wells 220 and 222 open at their ends at outlets 220' and 222' extending to the top surface 215 of the hydrogel 214 permitting flow of the drug sample through the channel of wells 220 and 222, with inflow and outflow of the drug sample from the hydrogel at outlets 220' and 222', and by which the hydrogel 214 may better mimic a blood vessel and its surroundings. Any device as described herein may comprise the channel structures depicted in FIGS. 3A and 3B. For example, the wells 220, 222, 224, and 226 of any of the hydrogels 14 or 114 of FIGS. 1A-1D and 2A-2B may be replaced with the channel structures depicted in FIGS. 3A and 3B.

The tissue sample may be any suitable tissue sample, and may be normal or diseased tissue, such as hyperplastic or cancerous tissue, as may be found in a tumor or cyst. In use, the hydrogel 14, 114, 214 is deposited over the tissue sample(s) as a liquid and then forms a gel. For example, a gelatin template, which is a gel at room temperature (e.g., 25° C.), and which melts at 37° C., is molded to define the wells or channels of the device. Tissue sample(s) are placed in the device, and the hydrogel is deposited in liquid form in the device over the tissue samples and around the gelatin form. The hydrogel is then allowed to gel and then is heated to 37° C. at which temperature the gelatin melts and can be washed from the wells. The hydrogel may be any biocompatible hydrogel that is a gel at 37° C., so long as the material can be applied to live tissue samples and gelled without significantly damaging viability of cells in the tissue. The hydrogel may be an ECM material, or a natural or synthetic polymeric material. By "biocompatible" in reference to a hydrogel, it is meant that the hydrogel, and the method of forming the hydrogel over the tissue samples as described herein is not substantially harmful to cell or tissue viability, such that cell or tissue viability can be maintained within the hydrogel for at least a short period of time sufficient to achieve the object of an assay as described herein. In the context of the present disclosure, the cell or tissue viability may be maintained within the hydrogel, for example and without limitation, for at least 24 hours, at least 36 hours, at least 48 hours, or at least 72 hours, including increments there between. The hydrogel may comprise buffers, such as phosphate buffered saline, or cell culture medium, such as serum-free, or serum-containing medium, e.g., as are broadly available commercially and/or as are broadly described in the literature. For example Dulbecco's Modified Eagle's Medium (DMEM) with 10% fetal bovine serum (FBS) may be used, essentially as described in the examples below.

The hydrogel may be formed from ECM, and may be a purified ECM product, such as purified collagen, such as type I collagen, for example as described below, or may be a mixture of collagen with other ECM components, such as those present in the tissue source of the collagen, or a complete ECM product, such as a collagen gel as described in. The terms "extracellular matrix" and "ECM" refer to a natural scaffolding for cell growth that is prepared by decellularization of tissue found in multicellular organisms, such as mammals and humans. ECM can be further processed by, for instance dialysis or cross-linking. ECM is a complex mixture of structural and non-structural biomolecules, including, but not limited to, collagens, elastins, laminins, glycosaminoglycans, proteoglycans, antimicrobials, chemoattractants, cytokines, and/or growth factors. In mammals, ECM often comprises about 90% collagen, in its various forms. The composition and structure of ECMs vary depending on the source of the tissue. For example, dermal, small intestine submucosa (SIS), urinary bladder matrix (UBM) and liver stroma ECM each differ in their overall structure and composition due to the unique cellular niche needed for each tissue.

Depending on how purified, ECM may relate to an extracellular matrix that retains activity of its structural and non-structural biomolecules, including, but not limited to, collagens, elastins, laminins, glycosaminoglycans, proteoglycans, antimicrobials, chemoattractants, cytokines, and/or growth factors, such as, without limitation comminuted ECM as described herein. The activity of the biomolecules within the ECM can be removed chemically or mechanically, for example, by cross-linking and/or by dialyzing the ECM. In one embodiment, the ECM has not been chemically cross-linked and/or dialyzed, meaning that the ECM has not been subjected to a dialysis and/or a cross-linking process.

In general, a method of preparing an ECM-derived gel requires the isolation of ECM from an animal of interest and from a tissue or organ of interest. In certain embodiments, the ECM is isolated from mammalian tissue. As used herein, the term "mammalian tissue" refers to tissue derived from a mammal, wherein tissue comprises any cellular component of an animal. For example and without limitation, tissue can be derived from aggregates of cells, an organ, portions of an organ, or combinations of organs. ECM may be isolated from a vertebrate animal, for example and without limitation, human, monkey, pig, cattle, and sheep. ECM may be isolated from any tissue of an animal, for example and without limitation, urinary bladder, liver, CNS, adipose tissue, small intestine, large intestine, colon, esophagus, pancreas, dermis, and heart.

Following isolation of the tissue of interest, decellularization is performed by various methods, for example and without limitation, exposure to hypertonic saline, peracetic acid, TRITON™-X, or other detergents. Decellularized ECM can then be dried, either lyophilized (freeze-dried) or air dried. Dried ECM can be comminuted by methods including, but not limited to, tearing, milling, cutting, grinding, and shearing. The comminuted ECM can also be further processed into a powdered form by methods, for example and without limitation, such as grinding or milling in a frozen or freeze-dried state.

To prepare solubilized ECM tissue useful in forming a hydrogel, comminuted ECM may be digested with an acid protease in an acidic solution to form a digest solution. As used herein, the term "acid protease" refers to an enzyme that cleaves peptide bonds, wherein the enzyme has increased activity of cleaving peptide bonds in an acidic pH. For example and without limitation, acid proteases can include pepsin and trypsin. The digest solution of ECM typically is kept at a constant stir for a certain amount of time at room temperature. The ECM digest can be used immediately or be stored at −20° C. or frozen at, for example and without limitation, −20° C. or −80° C. Next, the pH of the digest solution is neutralized, e.g., raised to a pH between 7.2 and 7.8, to produce a neutralized digest solution. The pH can be raised by adding one or more of a base or an isotonic buffered solution, for example and without limitation, NaOH or PBS at pH 7.4. The method may not include a dialysis step prior to gelation, yielding a more-complete ECM-like matrix that typically gels at 37° C. more slowly than comparable collagen or dialyzed ECM preparations. The solubilized and neutralized liquid can be introduced into the device comprising the solid tissue samples as described herein, and also retains more of the qualities of native ECM due to retention of many native soluble factors, such as, without limitation, cytokines. Where a gelatin form is used to incorporate channels in the hydrogel, the neutralized digest solution can be first gelled at room temperature, followed by incubation at 37° C. to melt the gelatin.

Synthetic polymers may be used to form the hydrogel of the devices described herein. Non-limiting examples of useful polymer compositions include: polyolefin (polyalkene), polyester, polycarbonate, polyanhydride, polyether, polyurea, polyurethane, polyketone, and fluoropolymers. Non-limiting examples of biocompatible (co)polymer compositions that have been established as useful in preparing cell growth matrices, include poly(ester urethane) urea (PEUU), poly(ether ester urethane)urea (PEEUU), poly(ester carbonate)urethane urea (PECUU) and poly(carbonate) urethane urea (PCUU). Useful (co)polymers further include: polymers comprising monomers of alpha-hydroxy acids; polylactides, such as poly(lactide-co-glycolide), poly(L-lactide-co-caprolactone), polyglycolic acid, poly(dl-lactide-co-glycolide), poly(l-lactide-co-dl-lactide); polyesters including polyhydroxybutyrate, polyhydroxyvalerate, polydioxanone and polyglactin; polylactones including polycaprolactone; polycarbonates, polyglyconate, poly(glycolide-co-trimethylene carbonate), poly(glycolide-co-trimethylene carbonate-co-dioxanone); and polyurethanes, poly (ester urethane) urea polymers. Block copolymers comprising poly(ethylene glycol) may be useful in the devices described herein. Many of the preceding polymer compositions are reverse-gelling, meaning they are a liquid at a first temperature and form a hydrogel when the temperature is raised. For example, the polymer composition may be selected such that it transitions from a liquid to a gel (e.g., has a Lower Critical Solution Temperature, or LCST) between 4° C. and 20° C. to form a gel at room temperature. The hydrogel is optionally not formed from a siloxane such as polydimethylsiloxane (PDMS). The hydrogel may preferably be an ECM gel, such as a collagen gel, an acid protease-solubilized ECM product as described above, or a commercial ECM product, such as MATRIGEL®.

To conduct the assays as described herein, a device as described herein is prepared or provided, and a drug sample is deposited into the well(s) of the device. The device is then incubated for a length of time suitable for diffusion of drug from the wells, but not extending beyond a time in which drug concentration becomes uniform throughout the hydrogel and viability of the cells is substantially reduced by way of the culture technique, as opposed to viability from action of the drug and/or cells of the tissue samples. Under suitable culture conditions, after a time period, cells will begin to migrate, and morphology of the tissue sample can diverge from native morphology. The assay therefore may be conducted over from six hours to one week, or even longer, depending on the culture conditions and the dosing conditions, for example over 6 hours, 8 hours, 12 hours, 18 hours, 24 hours, 36 hours, 48 hours, 60 hours, or 72 hours. The device may be placed in an incubator under any suitable conditions, such as from 35° C. to 38° C., for example at 37° C. in 5% $CO_2$. Drug samples may be placed in the well only once at the beginning of the assay, continuously, or intermittently over the duration of the assay. In reference to the open wells and channels described in FIGS. 1A-1D, 2A-2B, and 3A-3B, it may be preferable that the wells be configured as channels as depicted in FIGS. 3A and 3B, especially when continuous drug delivery is desired, as in mimicking IV perfusion.

Samples may be analyzed to determine the effect of the drug(s) by any useful method, such as, for example and without limitation, by live/dead staining, or immunofluorescence staining for Ki-67 and caspase 3 to quantify proliferation and apoptosis, for example by the methods described herein. The tissue samples may be evaluated in situ within the device, or they may be removed from the device. If removed from the device, the tissue samples may be analyzed by any suitable method, such as by staining, immunostaining, nucleic acid amplification, probe binding of nucleic acid sequences, or any combination thereof.

Any step described herein can be performed manually, e.g., by a pathologist or technician, or can be automated. For example, once a tissue sample is obtained and is embedded in the hydrogel of the device by a technician or pathologist, the device, in the form of a cartridge adapted as part of a system, is placed in a suitable location or receptacle in the automated system, drug sample is added to the well(s), and the system incubates the sample for a time period suitable for the assay. Once incubated, the system may add suitable dyes, binding reagents, indicators, or other reagent for identifying the viability of the cells (e.g., live/dead), or for identifying the presence of any biological marker (e.g., Ki-67 and caspase 3) and the cells may be imaged, and analyzed using suitable image-processing software or algorithms, or other computer-implemented method, to provide a useful output, such as a minimum concentration of a drug for inhibiting growth of a tumor sample. Embedding the sample in the tissue sample device may be automated by suitable robotic and fluidic equipment. As such, the device may be provided to an end-user as a kit, comprising the device without the tissue samples, and including a separate container, e.g., a vial or vessel, comprising the hydrogel, or ingredients for the end-user to prepare the hydrogel. The device, as provided without the hydrogel, may comprise suitable markings for locating two or more tissue samples, or a single, larger sample as described herein. A suitable system for automating the assay can be connected to a controller, such as a computer system as part of the system, or separately, for controlling the processing of the device, and for detecting and analyzing the tissue samples during or after completion of the incubation of the tissue sample in the presence of the drug. A person of ordinary skill in the fields of computer science and engineering can develop systems useful in automation of all or part of the processes described herein.

The assay may be part of a treatment of a patient having a tumor. In this treatment method, a biopsy of the tumor is taken from the patient, divided, for example, to produce 2, 3, 4, 5, 6, 7, 8, 9, etc. tissue sample pieces, or sliced to produce a single, large tissue sample, and the tissue sample is placed in the device and embedded in the hydrogel, essentially as described above. The device may have one, two, three, or more wells, and, where more than one well is used, different drugs may be placed in different wells, e.g., in the oppo configuration as described below, and the device is incubated to allow the drug(s) to diffuse. Suitable computation methods for determining diffusion of the drug in the hydrogel may be used to determine the concentration or dose of drug applied at any given position or tissue sample in the device, and the optimal effective dose for each drug tested is determined, for example as shown below in the examples. The optimal drug profile is then used to treat the patient. This assay uses only small amounts of tissue sample and drug, is relatively simple and fast, and effectively determines optimal dose for the particular patient based on realistic and inexpensive assay conditions. As with the patient-specific assay, the described method may be used to screen new drugs using the same methods, and tissue samples obtained either from patients, or animal models.

A therapeutic agent may be screened using the device and methods described herein. Non-limiting examples of therapeutic agents include: drugs, radioactive isotopes; viral particles and vectors including but not limited to oncolytic virotherapy agents; RNA based therapeutics including but not limited to antisense oligonucleotides, RNA interference (RNAi) agents and mRNA agents; living or dead microbiological treatments including but not limited to bacteria or any other microbe; and/or microrobots.

In the context of drugs useful in treating cancers, (chemotherapeutic drugs), the following is a non-exhaustive, and non-limiting list of examples of such chemotherapeutic drugs: abiraterone acetate, altretamine, amsacrine, anhydro vinblastine, auristatin, bafetinib, bexarotene, bicalutamide, BMS 184476, 2,3,4,5,6-pentafluoro-N-(3-fluoro-4-methoxyphenyl)benzene sulfonamide, bleomycin, bosutinib, busulfan, cachectin, cemadotin, chlorambucil, cyclophosphamide, 3',4'-didehydro-4'-deoxy-8'-norvincaleukoblastine, docetaxel, carboplatin, carmustine (BCNU), chlorambucil, cisplatin, cryptophycin, cyclophosphamide, cytarabine, dacarbazine (DTIC), dactinomycin, daunorubicin, decitabine dolastatin, doxorubicin (adriamycin), etoposide, etoposide phosphate, 5-fluorouracil, finasteride, flutamide, hydroxyurea, hydroxyureataxanes, ifosfamide, imatinib, irinotecan, liarozole, lonidamine, lomustine (CCNU), MDV3100, mechlorethamine (nitrogen mustard), melphalan, mitoxantrone, mivobulin isethionate, rhizoxin, sertenef, streptozocin, mitomycin, methotrexate, nilotinib, nilutamide, onapristone, oxaliplatin, paclitaxel, ponatinib, prednimustine, procarbazine, RPRI 09881, stramustine phosphate, tamoxifen, tasonermin, taxol, teniposide, topotecan, tretinoin, vinblastine, vincristine, vindesine sulfate, vinflunine, or pharmaceutically acceptable salts or esters thereof. Any chemotherapeutic drug or combination of drugs may be tested for safety and efficacy using solid tissue samples, or dispersed cells, according to the methods described herein.

EXAMPLES

To develop a more reliable tumor model that could mimic TME in vivo, one approach is to consider developing mimetic systems from an engineering perspective. The motivation behind this includes the knowledge that tumors are complex systems with different functional units such as different cell types, extracellular matrix (ECM), vasculature system, multiple chemical factors, etc. An engineered system offers many advantages for meaningful analyses of cancer progression as it can potentially mimic physiological relevant tumor-promoting mechanical forces such as shear stress from the dynamic flow in the vasculature, tension from the solid tumor, and stiffness variation of ECM. It might also mimic chemical factors such as chemotaxis due to nutrient diffusion and growth factor transduction, as well as hypoxia gradient due to oxygen diffusion limit. Moreover, cell interaction between tumor cells and cancer-associated fibroblast, endothelial cells, etc. are also considered relevant to metastasis, and, thus, having a system that can incorporate multiple cell types interacting with each other could be quite advantageous. All these factors are potentially able to be recreated and examined in tumor-on-a-chip approaches through integrated designs and approach. Engineering techniques have been developed that enable better mimicking of physiological environments on-chip systems. These approaches include the development of soft lithography, which has allowed microfluidic channels and dynamic flow systems to be fabricated and mimics physiological systems such as blood flow. Besides, 3D bioprinting has been able to print multiple cell types into ECM systems with high spatially precision. Also, computational models have contributed to these advances including studies in diffusion theory and fluid dynamics, for the development of tumor-on-a-chip systems that allow for high flexibility and multiple functionalities due to their rapid computational simulation with a diversity of parameters, at least to provide a rough prediction for multiple experimental results. Through these different techniques, a system can be designed that combines important factors of tumor progression. Even further, tumor-on-a-chip systems can be analyzed in conventional petri dish assays, which would then allow fluorescent staining and real-time measurements to observe cell motility, epithelial-to-mesenchymal transition (EMT), angiogenesis, and growth factor modulations.

To achieve the purpose of culturing tumor into a 3D environment, we applied 3D collagen type I scaffold for tumors to be embedded. We applied the same design in a second example, with double parallel microfluidic channels on both sides for initial drug injection, and tumors located in between the channels. This design satisfied several goals. Firstly, tumor fragments were embedded at the bottom of the collagen, thus partly isolated from the air, to create a mild hypoxia condition (The hypoxia level could be adjusted simply by changing collagen scaffold thickness). Secondly, the circular microfluidic channels on both ends could mimic the vessel system for drug perfusion. Drug injection through patient veins would cause drug delivery from a vessel system to local tissue through diffusion. This process was simulated in our device by perfusion of drug into the microfluidic channel and allow it to physically diffuse into the collagen scaffold, and eventually reach tumor samples. We also can coat endothelial cells in the channel to observe their behavior through drug delivery process. Thirdly, diffusion of drug would develop a smooth drug gradient, and each tumor sample would experience a different dynamic local drug concentration, which exactly met the requirement from tumor drug screening to test multiple drug doses.

Therefore, our design satisfied the necessary goals we proposed for 3D in vivo mimicking tumor drug screening design.

Before we could start tumor loading and drug screen, it is necessary to select the correct drug types and determine the drug diffusion profile. First of all, we decided to perform drug screening to breast tumors, with, as examples olaparib (PARP inhibitor), Camptothecin (Topo I inhibitor), cisplatin, doxorubicin, and/or newer drugs in development stage. However, for these initial experiments, we aimed to select drugs with the following criteria: a) The drug should be detectable so that we could determine its diffusion profile experimentally in the device. b) The drug should be well-studied and clinically applied so we could gain enough data for comparison with our experiments. c) We decided not only to test single drug effects but drug combinations. These criteria led us to the breast cancer drug combination lists approved by the Food and Drug Administration (FDA). Among these drug combinations, AC combination (Doxorubicin & cydophosphamide) is a well-known drug combination with a synergic effect in the primary treatment of breast cancer chemotherapy. Another advantage using doxorubicin is that doxorubicin molecules are autofluorescent with excitation wavelength at 480 nm & 296 nm.

Methods

Tumor preparation: All animal experiments were approved by the University of Pittsburgh IACUC. MDA-MB-231 cells were injected into the mammary fat pad of 3-4-week-old female nude immune-compromised SCID-Beige mice and the tumors were harvested 8 weeks after implantation. The tumors were stored in liquid nitrogen. Before drug testing, tumor samples were thawed and immediately sliced with a scalpel into roughly 2 mm³ (1 mm*1 mm*2 mm) fragments. Tumor sections close to the necrotic core and the surface were removed. Each fragment was divided into two 1 mm³ fragments, one for live/dead staining to ensure the fragment had over 70% viability. Fragments that were viable were embedded into the 3D ECM micro-systems for drug screening.

Tumor device fabrication: Building off our previous work (57), the device chamber was fabricated by cutting PMMA boards (TAP Plastic, 2.4 cm in thickness) into chamber walls (inner: 40*16 mm, outer: 44*20 mm) through a laser cutting system (Epilog, CO). Then the chamber was attached to a 50*22 coverslip with optical adhesive (NOA 81, Norland products Inc., NJ). The device was cured with UV for 2 min and rinsed with 70% ethanol under UV light for 2 h, then rinsed twice with 1×PBS to remove residual ethanol. The gelatin template was prepared, then positioned in the chamber. Three or five tumor samples were placed between the parallel channels, with equal distance between each sample, or any other locations for desired local dosing, based on our 1D simulation. Collagen with 3 mg/ml concentration (10% 10×PBS, high concentration collagen type I with corresponding concentration ratio, 1N NaOH=0.023*collagen, and DMEM+10% FBS) was injected into the chamber and covered the tumor samples. Then the device was maintained at room temperature for 30 min, followed by incubation at 37° C. for 30 min. The gelatin template was then removed with a syringe.

Doxorubicin drug gradient characterization: Doxorubicin (Selleckchem, in DMSO) was first diluted by DMEM+10% FBS to 100 mM, then injected into the left channel of one blank device (without the presence of tumor samples). The device was next imaged using confocal microscopy. Doxorubicin had an excitation/emission wavelength of approximately 480/560 nm. Images were captured moving spatially across the device from the left channel to right channel, at 1 mm intervals. The average intensity of the images (intensity of doxorubicin fluorescence) was determined through image analysis of the confocal microscope images (Axio Observer Z1 Microscope System, Zeiss). The sample was incubated at 37° C. for 24 h, then removed and another set of images was capture. A baseline intensity was also determined by imaging a blank device without the doxorubicin injection.

Viability test for tumor samples: Tumors embedded in the device were stained with 100 ml of CalAM+EthD-1 solution (adding droplets directly on top of tumors in the device) for 1 h, then rinsed with 1×PBS twice (10 min each). Next the device was imaged with a confocal microscope. This test though is destructive to tumor samples, so multiple samples were needed for Day 0 up to Day 6 for viability tests. For tumors cultured in 96-well plates, the media was removed, and 100 ml of CalAM+EthD-1 solution was added per well for 30 min staining followed by 1×PBS rinse twice (10 min each). Then the tumors were imaged with confocal microscopy. Images were then analyzed with ImageJ (ImageJ.nih.gov) to count green (live) and red (dead) cells. Viability was determined by their ratio.

1D-simulation of the drug profile: To demonstrate the feasibility of the model-based data-fitting approach, we simulated and predicted the diffusion profile of drugs through a simplified 1D diffusion equation. Since the double channels in our current design were parallel to each other, the diffusion profile along with the device was approximately parallel as well. We simulated the model by integrating the 1D diffusion equation:

$$\frac{\partial C_i}{\partial t} = D_i(x)\frac{\partial^2 C_i}{\partial x^2}$$

using a fixed time step forward Euler method, and $2^{nd}$ order center difference approximation to the Laplacian. The simulation used Matlab (ver. R2018b) (See, FIG. 4).

Tumor drug testing: Single drug testing: In the device, 30 μl of doxorubicin (100 μM) or 4-hydroxycyclophosphamide (Toronto Research Chemicals, dissolved in DMSO, 100 mM) diluted in DMEM+10% FBS was injected into one channel and the device was stored in a 5% $CO_2$ 37° C. incubator for up to three days. Every 12 h the device was taken out, the drug was removed from channel, and the media in the channels was replenished with fresh drug solutions. In the 2D 96-well control, 100 μl of doxorubicin/4-hydroxycyclophosphamide with a designated concentration was added per well. The samples were stored in the incubator for three days. The solutions were refreshed every 12 h.

Double drug testing: Opposite drug administration in the device: 30 μl of doxorubicin (100 μM) solution was injected into left channel, then 30 μl of 4-hydroxycyclophosphamide (100 mM) solution was injected into right channel. The solutions were refreshed every 12 h. Parallel drug administration in device: Mixture of doxorubicin (100 μM, final concentration) and 4-hydroxycyclophosphamide (100 mM, final concentration) was injected into left channel. The solutions were refreshed every 12 hours. Opposite/parallel drug administration in 96-well plates: Mixtures of doxorubicin & 4-hydroxycyclophosphamide with designed concentrations were added per well.

All samples were incubated for three days, removed, washed twice with PBS, and stained with CalAM and EthD-1 for viability imaging. The same approach was applied to cisplatin+paclitaxel, and paclitaxel+vincristine drug combinations.

Results

3D ECM microsystem design and validation: Intravenous drug delivery from the vasculature into local tissue depends on diffusion profiles of the individual compounds. To replicate this process, we created a 3D collagen type I scaffolding in which 5 tumor tissues (1 $mm^3$, derived from MDA-MB-231 human breast cancer cell line mouse xenografts) could be embedded (FIG. 5 (B)). We previously developed a micromilling technique to fabricate microfluidic channels directly in a 3D ECM microsystem. Circular microfluidic channels were incorporated on both ends to establish drug gradients that perfuse across the device and the tumor samples (FIG. 5 (B)). First, the clinically relevant breast cancer therapeutic drug adriamycin (doxorubicin) was tested to assess if drug diffusion can be reliably predicted in the 3D-collage scaffold. Doxorubicin (30 ml) was injected into the left channel of the device, and allowed to diffuse into the collagen scaffold for 24 h. As doxorubicin molecules are auto-fluorescent, direct determination of the diffusion was determined through confocal microscopy imaging (FIG. 6 (A)). Doxorubicin fluorescent signals were captured and intensity profiles were measured at 1 and 24 h. After 24 h (FIG. 6 (B)), an approximately linear concentration profile was obtained from the left to the right channel. This allowed a one dimensional simulation using Matlab, by applying Fick's second law in one dimension (1D), with the finite difference method as a simplified math model. The obtained diffusion profile was compared to a mathematically simulated diffusion profile predicted through diffusion equations. Notably, experimentally obtained values for the slope of the curve were not significantly different from mathematically modeled curves (FIG. 6 (C)). To further examine the accuracy of the 1D simulation in the 3D collage scaffold the rhodamine 6G diffusion profile was predicted by using rhodamine 6G diffusion coefficients and comparing these modeling results to experimentally obtained values. Reassuringly, the 6G rhodamine diffusion profile matched the simulation as well.

To test next drug responses of actual tumor tissues in the device, human breast tumor xenograft fragments were created by injecting MDA-MB-231 cells into nude mice. Tumor fragments were dissected into two pieces (1 mm³) and characterized for viability to exclude dead tissue samples prior to screening. In further detail, tumor fragments obtained from different regions of the same tumor showed heterogeneous viability suggesting intratumoral heterogeneity. For example, tumor fragments taken from closer to the core region showed lower viability, which could have been due to hypoxia given the rapid growth of the MDA-MB-231 xenograft. Not surprisingly, fragments closer to the surface displayed higher viability. To examine intratumoral heterogeneity in more detail, 22 tumor fragments from 2 different tumors (11 fragments/tumor) were taken and immediately examined for viability (CalAM+EthD-1). Most samples showed 70% viability or higher, while some others did not as they were taken too close from the tumor core. Because it was expected that this heterogeneity might inevitably bring inconsistency to tumor drug testing, tumor fragments were screened beforehand for viability by dividing each fragment in half and to ensure acceptable initial viability (>70% live cells).

3D ECM microsystems were prepared with DMEM+10% FBS to provide tumor samples with essential nutrients. To first examine tumor tissue survival over time, tumor tissue viability was examined up to six days with five tumor samples per device. Tumor samples were then analyzed with a live/dead stain (CalAM & EthD-1) and confocal microscopy (FIGS. 6 (D) and 6 (E)). To avoid autofluorescence from tumor tissue, its ECM, and the collagen scaffold we altered the analysis using two methods to determine cell viability. First, since tumor autofluorescence is rather uniform throughout the tumor, image processing software was used (ImageJ bundled with Java 1.8.0_172; imagej.nih.gov/ij/download.html) to subtract autofluorescence from tumor tissue images. Secondly, tumors were cut into smaller pieces, gently manually detached with tweezers and against the coverslip. That way, it was found that tumor samples maintained over 75% viability in the device compared to initial viability of the tumor being approximately 80% (FIG. 6 (D)). To get a better sense if tumor viability in the 3D ECM microsystem differs from the one found in conventional 1D methods, tumor pieces were seeded in a 96 well plate, immersed in media and analyzed in parallel. As FIG. 6 (E) shows, tissue viability varied from about 76%-95% in both methods, but was comparable over time.

Single drug screening: To better mimic dynamic in vivo diffusion profiles and to identify drug concentrations that would fit best with COMPUSYN algorithms, drug concentration simulation was used through Matlab coding to compare one-time dosing vs constant-flow dosing (replenish drugs every 12 hours) over three days. The one-fill mode will cause a drop of initial high dose at the left channel, and the multiple-fills mode will cause a continuous increasing dose over the whole device. The constant-flow dosing mode suggested that compared to one-time dosing, higher max/min dose differences occur especially after 72 and 48 hours compared to 24 hours, which is preferable for more accurate simulation and estimation of a dose-effect curve using COMPUSYN.

To next correlate simulation with tumor viability, five tumor samples were placed in the 3D collage scaffold and 30 ml of media containing 100 mM of doxorubicin was introduced into the left channel. To achieve a constant channel drug concentration and match the simulation of constant-flow mode, drug containing media was replenished every 12 h. As a control, five tumor samples were placed individually in 96-well plates, and treated directly with 100 ml media (DMEM+10% FBS) with doxorubicin (every 12 hours) doses corresponding to a 48 h drug concentration simulated by Matlab for each tumor piece in the 3D device. The 48 h drug concentration was chosen to create a comparable dosing scheme between the 2 devices. After three days, all 10 samples (device and 96-well plate) were analyzed by live/dead staining and tissue viability was determined (FIG. 7A). As expected, a dose-dependent decrease in viability that correlated with the drug dose gradient was observed in both 2D controls as well as 3D ECM microsystem. Notably, the 3D ECM microsystem samples showed lower viability compared to 2D controls. As a reference, tumor samples from the 3D ECM microsystem were also analyzed for proliferation and apoptosis by immunofluorescence staining for Ki-67 and caspase 3, respectively. As expected, a dose-dependent increase in Ki-67 (proliferation) and decrease in caspase 3 (apoptosis) was observed, which was quantified and consistent with the live/dead staining results (FIG. 7B). Doxorubicin intrinsic fluorescence decreased as well across the spatially distributed samples, which correlated with the drug simulation analysis (FIG. 6 (A-C)).

Tumor viability during combination treatment: Drug synergism is an essential determinant in evaluating drug combination therapies. The advantage of synergistic drug effects, when compared to additive ones, is that a specific drug ratio generates higher effects than the combined individual drug responses (additive). Thus, drug synergism is a desired factor in evaluating combinatorial drug schemes. The Chou-Talalay method is frequently used to determine if two drugs act synergistic, additive or antagonistic. This method uses the combination index (CI) as a readout. Here, CI values, where CI<1 marks synergistic, CI=1 additive and CI>1 antagonistic drug effects, were calculated using COM-PUSYN software that is based on the Chou-Talalay method (Chou T-C. Drug combination studies and their synergy quantification using the Chou-Talalay method. Cancer research 2010; 70(2):440-6). The power of this method lies in determining optimal (less toxic) and efficacious drug ratios for combination treatments. In general, CI analyses are done in vitro using cell lines which allow testing of many different drug concentrations, but often lack in vivo reproducibility.

To test the feasibility of the 3D ECM microsystem, a drug combination was chosen that is commonly used to treat breast cancer: doxorubicin and cyclophosphamide act synergistically to kill tumor cells through different mechanisms. Doxorubicin kills cells by intercalation of DNA, topoisomerase II inhibition and free radical formation. Cyclophosphamide metabolites (e.g., 4-hydroxycyclophosphamide) mediates cell death by alkylating and crosslinking DNA in cancer cells. Four sample setups, essentially as presented in FIGS. 3A and 3B, were used to analyze the known synergistic effect of both drugs in the 3D ECM microsystem: doxorubicin alone (denoted as doxo), 4-hydroxycyclophosphamide alone (denoted as cyclo), doxorubicin and 4-hydroxycyclophosphamide in opposite directions (denoted as oppo), and both drugs diffusing in the same direction (denoted as para for parallel). For oppo, doxorubicin and 4-hydroxycyclophosphamide were injected from the left and right channels, respectively; and for para, both drugs were injected from the left channel. Similar to the one drug screening approach, 96-well controls were prepared, with drug doses matching 48 h dosing in the 3D ECM microsystem. In the 3D device, the concentration of the drugs at each tumor sample location was again determined through 1D simulation as before. The simulations revealed that compared to doxorubicin, 4-hydroxycyclophosphamide (277 g/mol) diffused faster than doxorubicin (543 g/mol), as expected with its lower molecular weight. Based on this and the median effect dose (Dm) of doxorubicin being previously reported as much lower than 4-hydroxycyclophosphamide for MDA-MB-231 cell treatment, we selected 100 mM of doxorubicin and 100 mM of 4-hydroxycyclophosphamide as the initial injection dose for each channel. Single drug treatments showed reduced tumor viability (1-effect) as the drug dose increased in the 96 well control and 3D ECM microsystem (FIGS. 8B (C) and (D)).

Referring to FIG. 9, Single drug screening data were plotted with the drug-effect curve and the median-effect curve. The drug effect curve was a direct plot of effect (fraction of cells affected, fa) vs. dose applied. The median-effect curve was plotted according to the median-effect equation, m, or the dynamic order that denotes the shape of dose-effect curve. Here, m was set as m<1 for all cases and indicates flat sigmoidal curves. The value of r is the correlation coefficient of the median-effect plot, which indicates how experimental data agreed with the theoretical prediction, or more precisely, with mass-action law. For in vitro experiments, r>0.95 are generally considered good for reliability. All data shown here passed this test, indicating acceptable precision for our experimental setup.

As expected, treatment with both drugs at the same time in para showed lower tumor tissue viability than either of the single drugs alone, which indicated that the addition of either drug increased the overall effect (FIGS. 8A (A) upper part, 8B (C) and (D)). In both oppo treatment schemes, 2D and 3D, the tissue viability after drug combination was dominated by the highest dose of doxo (FIGS. 8 (A) lower part, 8 (E) and 8 (F)). For the 3D ECM microsystem this suggests that the initial increase in tissue viability was due to a rapid drop of the dominating doxo effect, and that the subsequent decrease was mainly caused by synergistic combination effect of doxo and cyclo. The tissue viability curve (for both 2D control and 3D device) fluctuated from one side to the other, and reached a local minimum at double median dosing in the 3D ECM microsystem.

Comparison of synergistic and antagonistic combination indices in 2D and 3D: Analyzing the CI values (FIGS. 8A (A) and (B), and placed below each combination data point FIGS. 8B (C) to 8C (F)), it was noticed that while CI values of 2D and 3D analyses were mostly comparable in para and oppo, some subtle differences stood out. For example, the 2D midpoint CI value for para treatment (doxo & cyclo) started at 0.88 for high doses of doxo and cyclo and decreased to 0.46 for median doses, and then increased to 1.65 for low doses, suggesting better synergism, at midpoint (FIG. 8B (C)). Similar trends with a 2.4-fold lower CI value of 0.19 was observed in the para 3D ECM microsystem (FIG. 8B (D)). Importantly, for oppo combinations, maximum synergy occurred at "double-median" dosing in both the 2D control with a CI value of 0.53 and more convincingly in the 3D ECM microsystem with a CI value of 0.19 (FIG. 8C (E,F)). This suggests that the dynamic drug delivery in the 3D ECM microsystem provides a more robust synergy effect compared to the 2D analysis.

To examine a broader applicability of the 3D ECM microsystem, another drug combination common in breast cancer treatment was used: cisplatin and paclitaxel (cis & pac). For this drug combination, the diffusion coefficient for cisplatin and paclitaxel were calculated based on the assumption that the diffusion coefficient is inversely proportional to molecular weight. This assumption applies more precisely when drug molecules are similar in structure, and their molecular weight is not different by orders of magnitude. After the diffusion coefficients for both drugs were determined, a 1D diffusion simulation was implemented to determine the local drug concentration for cisplatin and paclitaxel. Since paclitaxel has a higher molecular weight, it diffused much slower than cisplatin in collagen. Unlike the doxo & cyclo combination, the clinical outcomes using this drug combination are mixed for drug synergy and effectiveness. While one study reported a 85% response rate with the cis and pac combination treatment, an only 21% response rate was found in another similar study. As before, drug diffusion profiles were determined for cis and pac individually, before viability and CI were examined. As shown in FIGS. 10A-10H, similar trends although less distinct were observed as for the doxo & cyclo combination, with a dominance of high cis doses in viability and lower midpoint CIs in the 3D ECM microsystem compared to the 2D control. As expected, given the clinical outcomes mentioned above, CI values were overall higher than found with the doxo & cyclo combination.

In further detail, as shown in FIG. 10B an optimal synergistic CI was observed at double-median dosing with CI=0.4~0.6. This synergistic effect is less than when compared to doxo & cyclo, which showed a CI of 0.19. For control samples (2D), the synergistic effect occurred at "double-high" and "high-cis and low-pac" dosing, while for the 3D device, neither end showed stable synergy, and the CI value fluctuated almost randomly. This might be due to the combination of cisplatin with paclitaxel, which can result in a rather unstable drug interaction in breast cancer treatment. However, the CI minimum point at "double-median" dosing indicated there might be an appropriate combination that showed reasonable synergy.

Lastly, a known antagonistic drug combination (paclitaxel and vincristine) was examined. Indeed, both combination curves showed significantly different profiles. For the para combination in 2D and 3D (grey lines in FIGS. 11A and 11B), the tumor viability was relatively high and stable even with an increasing dose of both drugs, with CI values. In oppo combinations, tissue viability at both ends (high pac or high yin) was lower and only one of the two drugs affected the response as the other drug, as observed in the diffusion simulation, could not effectively diffuse to the far end. This finding is an important distinction compared to the 2D model as in in vivo diffusion through the ECM defines drug efficacies and thus the 3D ECM microsystem provides a more accurate resemblance of drug effects.

Comparing then the midpoint para and oppo CI values for these 3 drug combinations (FIG. 11E) showed a stronger synergistic effect for the doxo & cyclo compared to cis & pac, while pac & yin presented an antagonistic effect. The CIs identified for the 3D ECM microsystem were comparable to CIs found in the 2D system. However, 3D CIs demonstrated lower CI values for the synergistic drug combinations, where the dox & cyclo CI was distinctively lower than the cis & pac CI, compared to the 2D analysis where both CIs appeared similar, thus better reflecting reported success of both combinations in human trials.

In summary, we introduce a novel 3D collagen tumor-on-a-chip approach with microfluidic channels applicable to combinatorial drug screening. The device permits 3D collagen-embedded tumor samples to be rapidly evaluated for drug sensitivity, employing drug diffusion profiles from vessel-mimicking channels, which simulate in vivo dynamic drug delivery. Based on mathematical simulations of drug diffusion profiles, local drug concentrations for each tumor sample in the 3D ECM microsystem were determined in a time dependent manner and applied to the 2D controls. Comparison between the 3D ECM microsystem and the commonly-used 2D 96-well approach confirmed the appropriateness of the 3D ECM microsystem that provides a much needed physiological-relevant experimental environment, in determining tissue viability, useful drug ratios and combination indices. Within a tissue, concentration gradients exist not only for oxygen, pH, nutrients and effector molecules, but also for drugs. Therefore, proximity of a blood vessel and ECM compositions are important factors determining drug concentrations in tumor tissues. The 3D ECM microsystem described herein helps to overcome these hurdles by offering blood vessel like structures (channels) embedded in collagen and diffusion gradients. Besides single drug gradient generation, we specifically designed and examined parallel-dosing and opposite-dosing strategies. Thus, the parallel setup mimicked intravenous chemotherapy delivery as a simplified version. As the opposite setup does not represent any in vivo application specifically, it offers an efficient way to test drug combinations in different dose ratios. In addition, we presented evidence here that the placement of 5 tumor pieces in series between two channels enables reliable testing of drug combinations to derive relevant drug ratios and thus, combination indices.

While 3D cell culture models, such as organoids, allow cell-to-ECM contact, they fail to reflect intratumoral heterogeneity. For example, fibroblasts, adipocytes, and immune cells a part of the tumor microenvironment (TME) and modulate the response of cancer cells to chemotherapies and targeted therapies through production of secreted factors. Therefore, analyzing tumor tissue that contains all TME cell types is necessary for valuable drug screening. We provide evidence that tumor tissues show decent viability up to 6 days. However, while that can be useful for some research purposes, in drug sensitivity testing such long time periods are not advisable, as prolonged interactions of tumor cells with the collagen scaffold induces cells to migrate out of the tumor that way resulting in different drug responses found in tumors with intact architecture. Another important factor requiring terse analysis time comes from the relative short viability of immune cells ex vivo, compared to cancer cells.

Intratumoral heterogeneity is also a result of clonal heterogeneity that influences drug responsiveness and has been addressed by emerging computational prediction models used to optimize cancer therapies. Intertumoral heterogeneity which describes genomic differences of the same cancer between two or more patients as well as clonal differences of metastases within one patient, is an equally pressing issue difficult to address in conventional drug screening approaches. Clearly, the 3D ECM microsystem presented here offers a personalized way to screen for effective drug combinations of the tested tissues.

Comparisons of time-dependent effects or dosing frequencies offer important pharmacological insight into how dosing regimens influence diffusion profiles, drug dosing range, and can lead to variations in drug treatment outcomes. For example, comparisons between the 2D and the 3D ECM microsystem showed that all four different drug application methods generated similar trends with dose-effect patterns in 2D and the 3D ECM microsystem. However, absolute cell death amounts differed between 2D and 3D, probably due to differences in the actual drug delivery profile over time: constant dosing in 2D vs. dynamic dosing 3D. In the control (96-well plates), tumor fragments were soaked in drugs, and thus experienced constant drug dosing, with 12 h replenishing over a three day period. In the 3D device, the tumor fragments were exposed to drugs through diffusion in the 3D ECM microsystem and experienced a dynamic and nonlinearly increasing dose profile, which is physiological more relevant as drug delivery in 2D. Therefore, in vitro drug screening by constant dosing is an overly simplified model that provides an inaccurate model of in vivo drug treatment. With the development of computational models and accuracy in simulations, a more reliable in vitro reference can be provided. Our study is merely a first step in dynamic diffusion simulation, but already identifies different drug effects especially in combination index (CI) values. For example, our Matlab simulation in 1D applying Fick's second law was a simplified tool to calculate spatiotemporal distribution of all drugs in the device, while a 3D simulation optimized by experimental data is preferable for more accurate determination in the future.

Other advantages of the 3D ECM microsystem are:
1) Ease of experimental manipulation: single dosing for the channels for each five-tumors in the device is easier than diluting and combining drug doses multiple times as required for the traditional 2D approach.
2) Low drug consumption: the micrometer scaled fluidic system requires only small volumes of reagents. As some drugs (especially new drugs in development) are expensive or initially only synthesized in small batches, our approach provides useful insight early in the drug development process.

In conclusion, we developed an effective and convenient new 3D collagen tumor-on-a-chip approach that offers microfluidic channels to mimic tumor vasculature in vivo for drug screening and a cancer appropriate ECM. Our device enables 3D embedded tumor samples to be examined with single/double drug combinations in a physiologically meaningful way as it enables drug diffusion through the ECM, which simulates in vivo dynamic drug delivery. The 3D ECM microsystem can be adapted depending on individual ECM requirements, availability of tumor tissues, etc. to provide personalized patient treatment.

Having described this invention above, it will be understood to those of ordinary skill in the art that the same can be performed within a wide and equivalent range of conditions, formulations and other parameters without affecting the scope of the invention or any embodiment thereof.

What is claimed:

1. A device comprising:
a containment structure comprising a base and one or more walls and configured to hold a hydrogel therein;
a biocompatible hydrogel contained within the containment structure, the biocompatible hydrogel defining a plurality of wells configured to retain a therapeutic agent, the plurality of wells formed in the hydrogel, and wherein the hydrogel is configured to allow for diffusion of the therapeutic agent thereby forming a concentration gradient of the therapeutic agent within the hydrogel; and
a live, solid tissue sample embedded in the hydrogel and spaced apart from the first well,
wherein the concentration gradient allows for determination of an effective dose of the therapeutic agent based on a determination of an effect of the therapeutic agent on the tissue sample.

2. The device of claim 1, wherein the tissue sample is a contiguous tissue sample comprising a first portion and a second portion, that is arranged within the hydrogel so that the first portion is a first distance from the plurality of wells, and the second portion is a second distance from the plurality of wells that is greater than the first distance from the plurality of wells.

3. The device of claim 1, comprising two or more tissue samples spaced at different distances from the plurality of wells.

4. The device of claim 1, wherein each of the plurality of wells is the second well is a larger distance from another well the first well than from the tissue sample any of the two or more tissue samples.

5. The device of claim 1, wherein the tissue sample is arranged between the plurality of wells.

6. The device of claim 1, wherein the hydrogel comprises at least three wells spaced around the tissue sample or samples.

7. The device of claim 1, wherein at least one of the plurality of wells is elongated.

8. The device of claim 7, wherein at least one of the plurality of wells is a slot or channel.

9. The device of claim 1, comprising a therapeutic agent in at least one of the plurality of wells.

10. The device of claim 1, configured as a cartridge for use in an automated system for incubating and/or analyzing the tissue sample.

11. The device of claim 1, wherein at least one of the plurality of wells comprises a channel embedded within the hydrogel having outlets extending to a surface of the hydrogel.

12. The device of claim 1, wherein the tissue sample is a biopsy obtained from a human or veterinary patient.

13. The device of claim 1, wherein the tissue sample is a sample of an abnormal tissue mass.

14. The device of claim 1, wherein the hydrogel comprises an extracellular matrix material.

15. A device comprising:

a biocompatible hydrogel defining at least a first well configured to retain a therapeutic agent, the at least first well formed in the hydrogel, wherein the hydrogel is configured to allow for diffusion of the therapeutic agent thereby forming a concentration gradient of the therapeutic agent within the hydrogel; and a live, solid tissue sample embedded in the hydrogel and spaced apart from the first well, wherein the concentration gradient allows for determination of an effective dose of the therapeutic agent based on a determination of an effect of the therapeutic agent on the tissue sample.

\* \* \* \* \*